(12) United States Patent
Okairi et al.

(10) Patent No.: US 9,765,296 B2
(45) Date of Patent: Sep. 19, 2017

(54) METHOD FOR PREPARING PLURIPOTENT STEM CELLS

(71) Applicant: OTSUKA PHARMACEUTICAL FACTORY, INC., Tokushima (JP)

(72) Inventors: Risa Okairi, Tokushima (JP); Masuhiro Nishimura, Tokushima (JP); Tamaki Wada, Tokushima (JP)

(73) Assignee: OTSUKA PHARMACEUTICAL FACTORY, INC., Tokushima (JP)

( * ) Notice: Subject to any disclaimer, the term of this patent is extended or adjusted under 35 U.S.C. 154(b) by 0 days.

(21) Appl. No.: 14/913,707

(22) PCT Filed: Sep. 3, 2014

(86) PCT No.: PCT/JP2014/004524
§ 371 (c)(1),
(2) Date: Feb. 23, 2016

(87) PCT Pub. No.: WO2015/033558
PCT Pub. Date: Mar. 12, 2015

(65) Prior Publication Data
US 2016/0215258 A1    Jul. 28, 2016

(30) Foreign Application Priority Data

Sep. 4, 2013 (JP) ................................ 2013-182945
May 16, 2014 (JP) ................................ 2014-102539

(51) Int. Cl.
*C12N 5/074*  (2010.01)
*C12N 5/0775* (2010.01)
*A61K 35/28*  (2015.01)

(52) U.S. Cl.
CPC ............ *C12N 5/0607* (2013.01); *A61K 35/28* (2013.01); *C12N 5/0663* (2013.01); *C12N 2506/1353* (2013.01); *C12N 2506/1384* (2013.01)

(58) Field of Classification Search
None
See application file for complete search history.

(56) References Cited

U.S. PATENT DOCUMENTS

| | | | | |
|---|---|---|---|---|
| 2010/0093053 | A1* | 4/2010 | Oh .................. | C12N 5/0062 435/176 |
| 2011/0070647 | A1  | 3/2011 | Dezawa et al. | |
| 2012/0244129 | A1  | 9/2012 | Dezawa et al. | |
| 2013/0260461 | A1  | 10/2013| Kobayashi et al. | |

FOREIGN PATENT DOCUMENTS

| | | | |
|---|---|---|---|
| JP | 5185443 | B2 | 4/2013 |
| WO | 2006/085612 | A  | 8/2006 |
| WO | 2008/150001 | A  | 12/2008 |
| WO | 2011/007900 | A  | 1/2011 |
| WO | 2012/063870 | A  | 5/2012 |
| WO | 2012/133942 | A1 | 10/2012 |

OTHER PUBLICATIONS

International Search Report issued with respect to application No. PCT/JP2014/004524, mail date is Dec. 16, 2014.
International Preliminary Report on Patentability issued with respect to application No. PCT/JP2014/004524, mail date is Mar. 8, 2016.
Kazutoshi Takahashi et al., "Induction of Pluripotent Cells from Mouse Embryonic and Adult Fibroblast Cultures by Defined Factors", Aug. 25, 2006, pp. 663-676, Cell 126.
Kazutoshi Takahashi et al., "Induction of Pluripotent Stem Cells from Adult Human Fibroblasts by Defined Factors", Nov. 30, 2007, pp. 861-872, Cell 131.
Masato Nakagawa et al., "Generation of induced pluripotent stem cells without Myc from mouse and human fibroblasts", Jan. 2008, pp. 101-106, Nature Biotechnology, vol. 26.
Marius Wering et al., "c-Myc is Dispensable for Direct Reprogramming of Mouse Fibroblasts", Jan. 2008, pp. 10-12, Cell Stem Cell 2.
Yasumasa Kuroda et al., "Unique multipotent cells in adult human mesenchymal cell populations", May 11, 2010, pp. 3639-8643, Proc Natl Acad Sci USA, vol. 107, No. 19.
Wakao et al., "Regenerative Effects of Mesenchymal Stem Cells: Contribution of Muse Cells, a Novel Pluripotent Stem Cell Type that Resides in Mesenchymal Cells", Cells, vol. 1, pp. 1045-1060, 2012.
Cesarz et al., "Spheroid Culture of Mesenchymal Stem Cells", Stem Cells International, vol. 2016, pp. 1-11, 2016.

(Continued)

*Primary Examiner* — David Berke-Schlessel
(74) *Attorney, Agent, or Firm* — Greenblum & Bernstein, P.L.C.

(57) ABSTRACT

An object of the present invention is to provide a method capable of inexpensively and conveniently preparing cells having pluripotency and a very low risk of tumorigenic transformation. The cells having pluripotency and a very low risk of tumorigenic transformation can be prepared by suspension-culturing mammalian mesenchymal stem cells such as human mesenchymal stem cells from bone marrow (hMSC-BM) and human adipose tissue-derived mesenchymal stem cells (hAT-MSC) (also referred to as "human adipose-derived stem cells [hADSC]"), 7 types of human adherent mature cells (human hepatocyte cells [hHEP cells], human umbilical vein endothelial cells [HUVEC cells], human dermal lymphatic microvascular endothelial cells [HMVEC cells], human epidermal keratinocyte cells [NHEK cells], human bronchial epithelial cells [NHBE cells], human melanocyte cells [NHEM cells], and human smooth muscle cells [UASMC cells]), and 3 types of human adherent precursor cells (human dermal fibroblast cells [NHDF cells], human skeletal muscle myoblast cells [HSMM cells], and human osteoblast cells [NHOst cells]) to form cell masses (spheroids).

4 Claims, 23 Drawing Sheets

(56) References Cited

OTHER PUBLICATIONS

Wang et al., "3D Spheroid Culture System on Micropatterned Substrates for Improved Differentiation Efficiency of Multipotent Mesenchymal Stem Cells", Biomaterials, vol. 30, pp. 2705-2715, published online Feb. 12, 2009.
Guo et al., "Epigenetic Changes of Mesenchymal Stem Cells in Three-Dimensional (3D) Spheroids", J. Cell. Mol. Med., vol. 18, No. 10, pp. 2009-2019, 2014.
Cheng et al., "Short-Term Spheroid Formation Enhances the Regenerative Capacity of Adipose-Derived Stem Cells by Promoting Sternness, Angiogenesis, and Chemotaxis", Stem Cells Translational Medicine, vol. 2, pp. 584-594, published online Jul. 11, 2013.
Cheng et al., "The Influence of Spheroid Formation of Human Adipose-Derived Stem Cells on Chitosan Films on Stemness and Differentiation Capabilities", Biomaterials, vol. 33, pp. 1748-1758, published online Dec. 9, 2011.
Search Report issued in European Patent Office (EPO) Patent Application No. 14842674.5, dated Feb. 15, 2017.

\* cited by examiner

[Figure 1]
Nanog
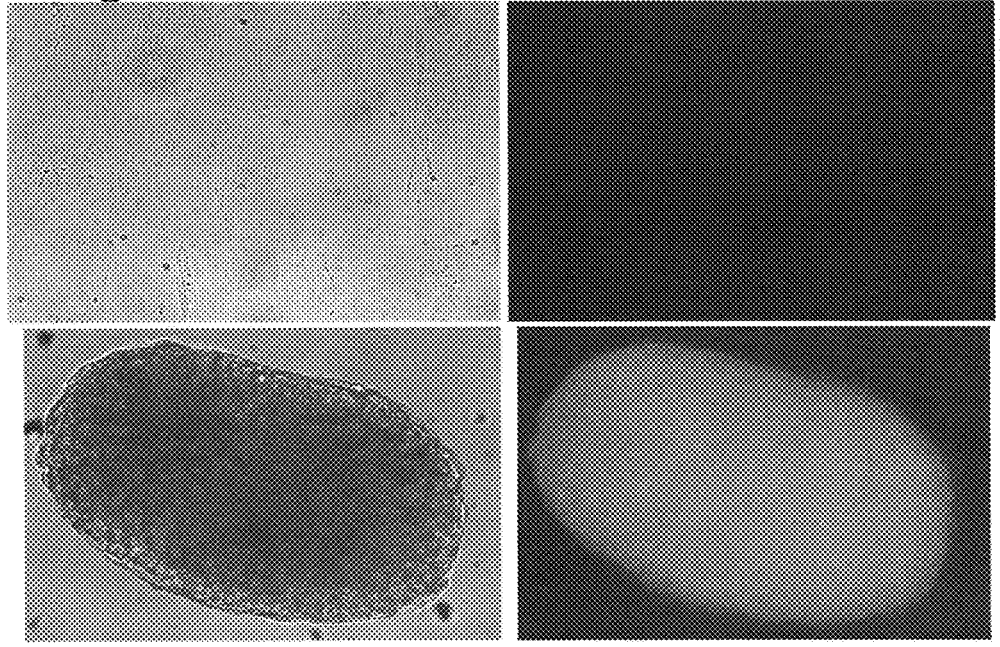
[Figure 2]
Oct3/4
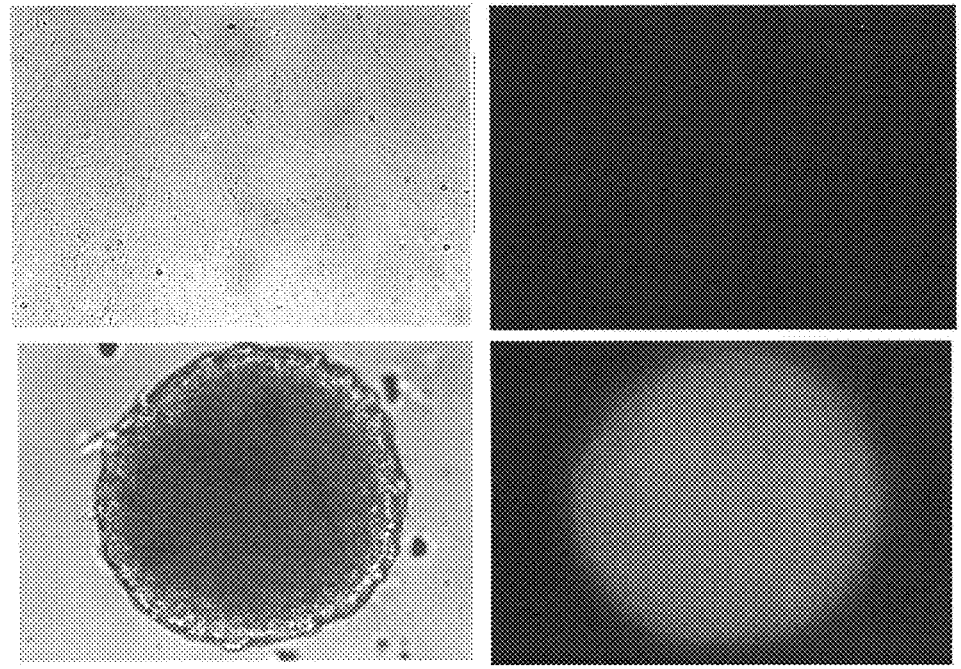

[Figure 3]
SOX2
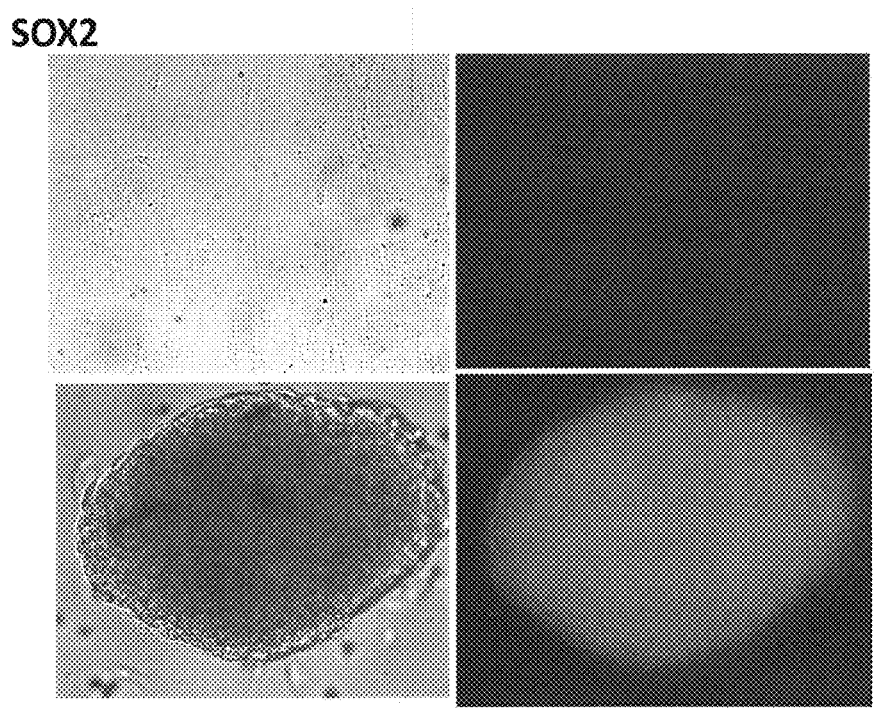

[Figure 4]
SSEA3
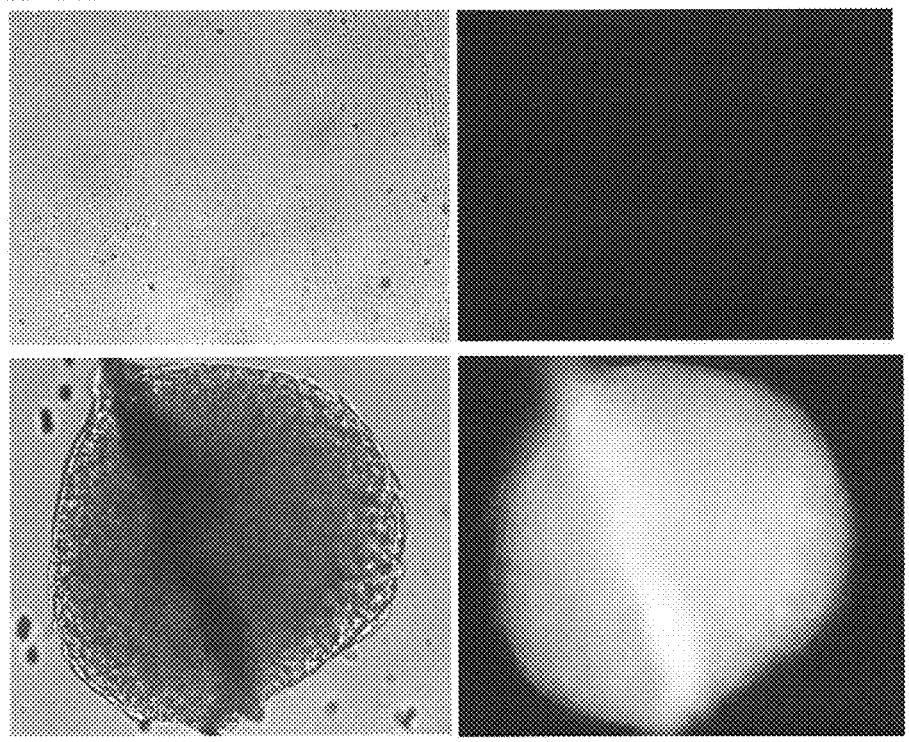

[Figure 5]
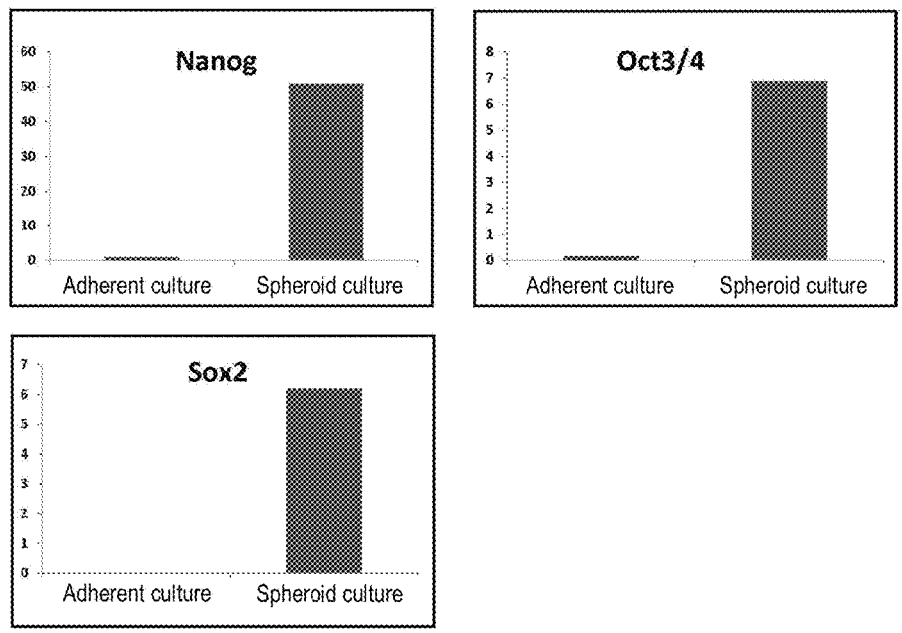
[Figure 6]
Nanog
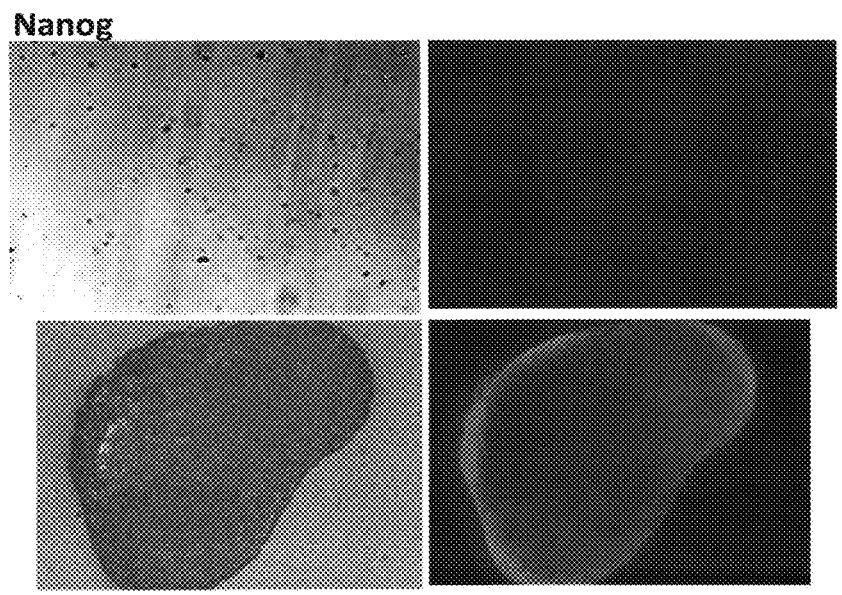

[Figure 7]
Oct3/4
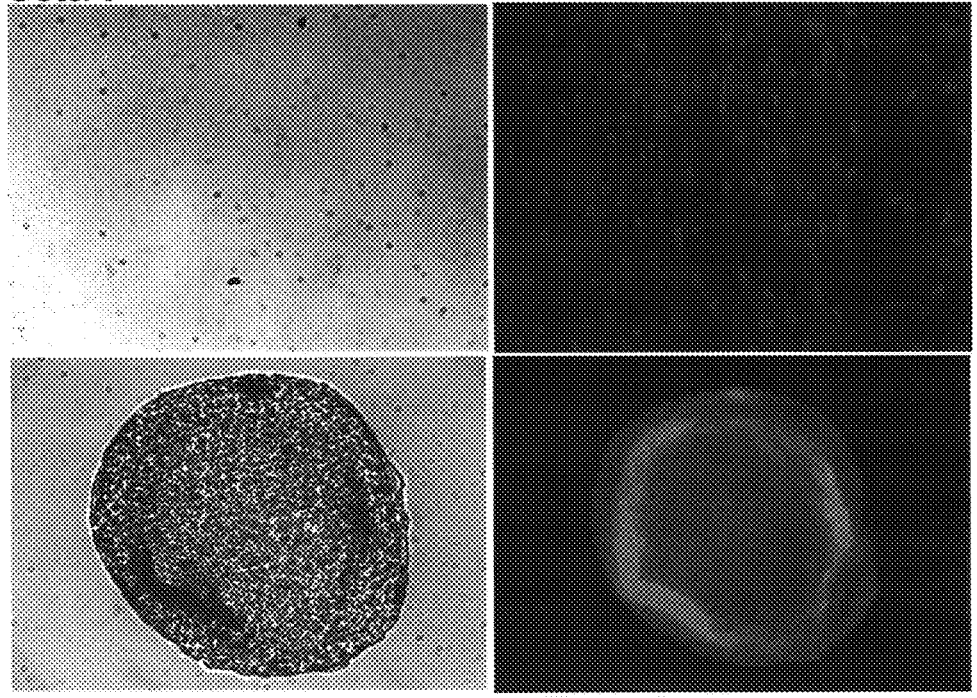
[Figure 8]
SOX2
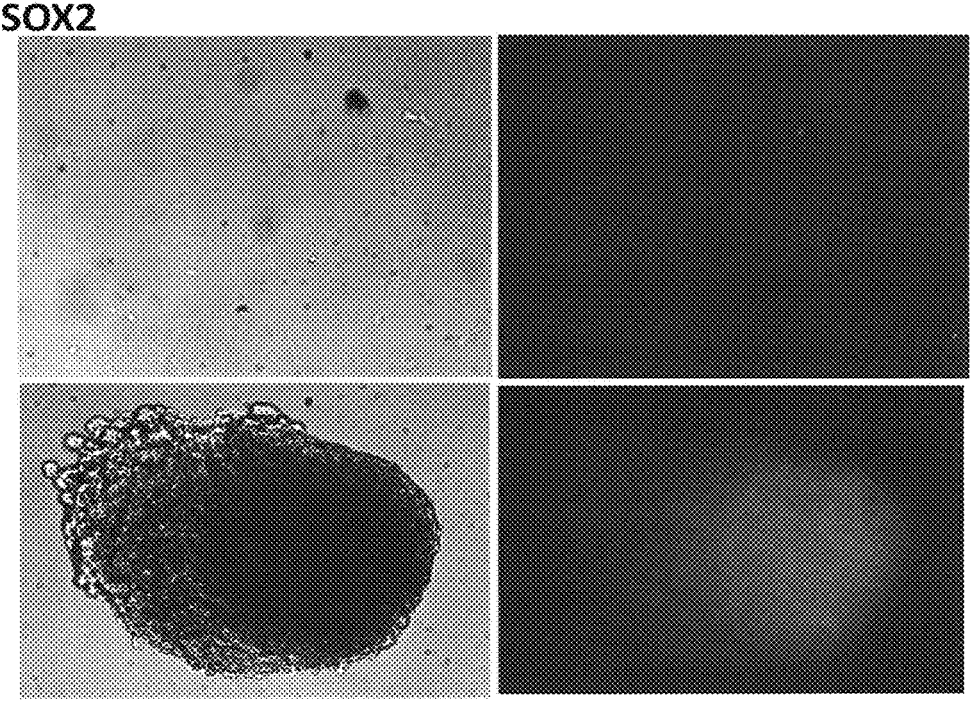

[Figure 9]
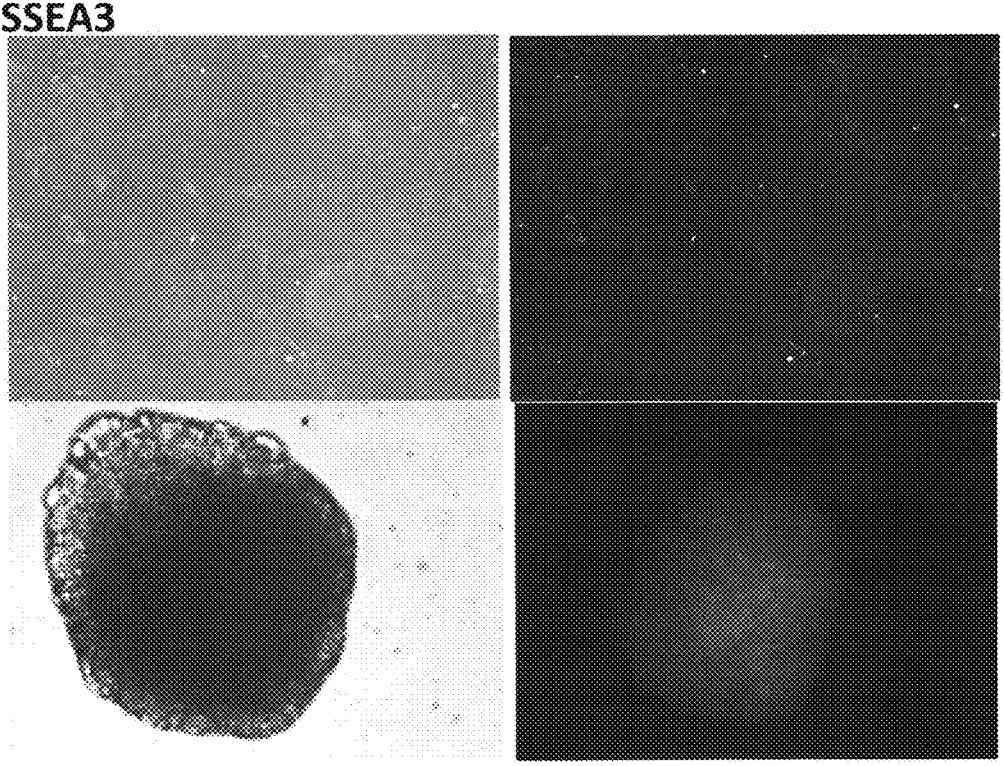

[Figure 10]
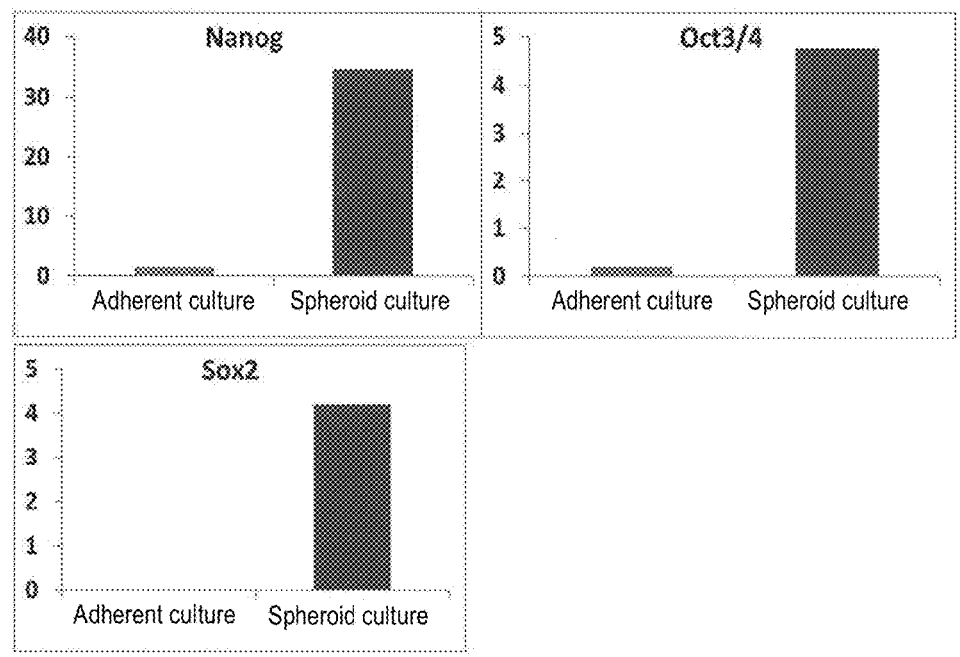

[Figure 11]
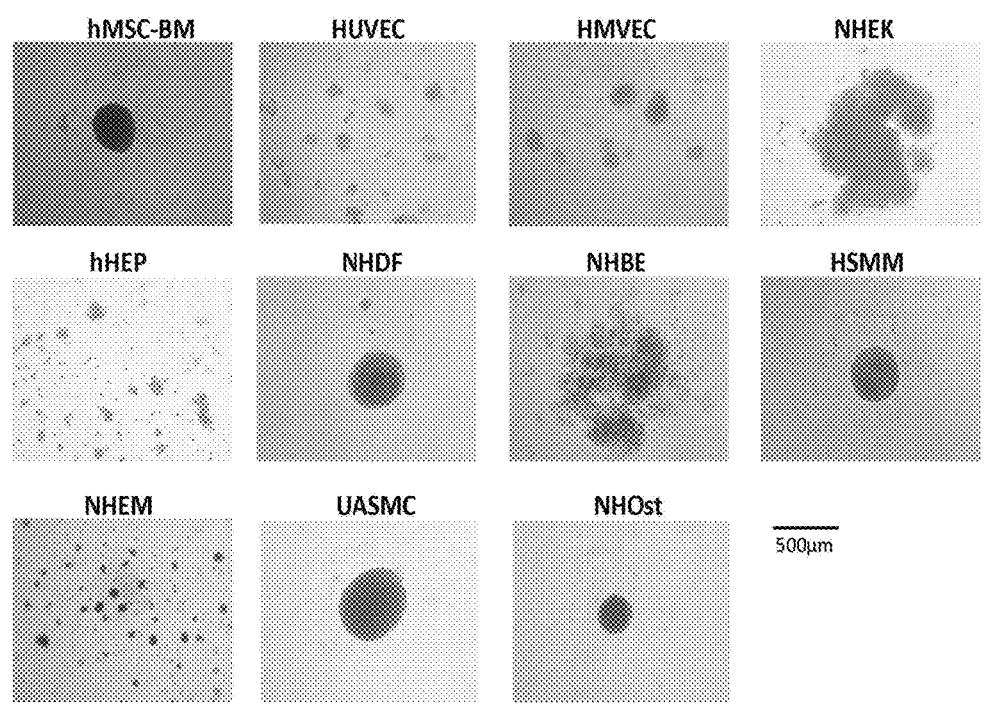

[Figure 12]
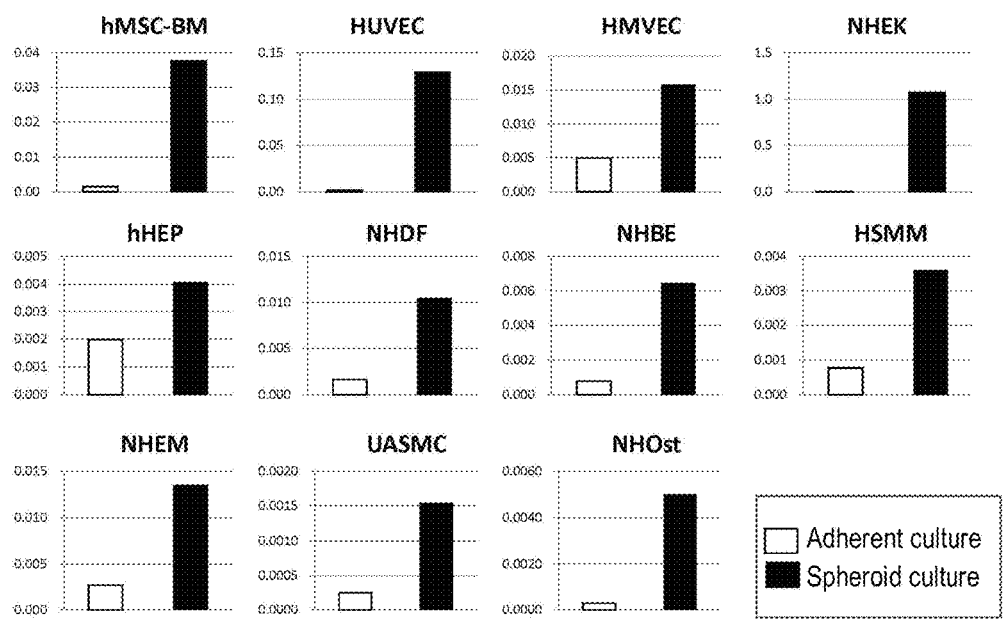

[Figure 13]
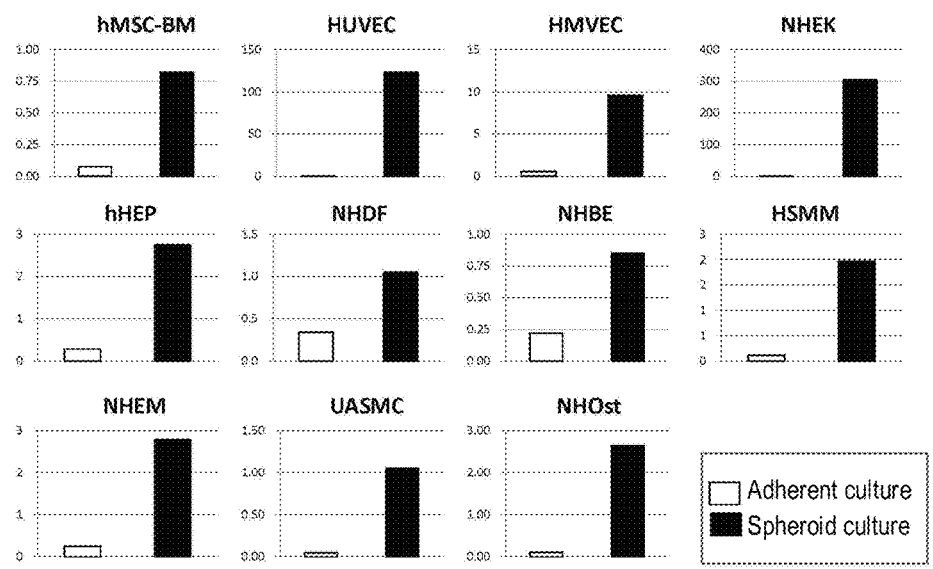

[Figure 14]
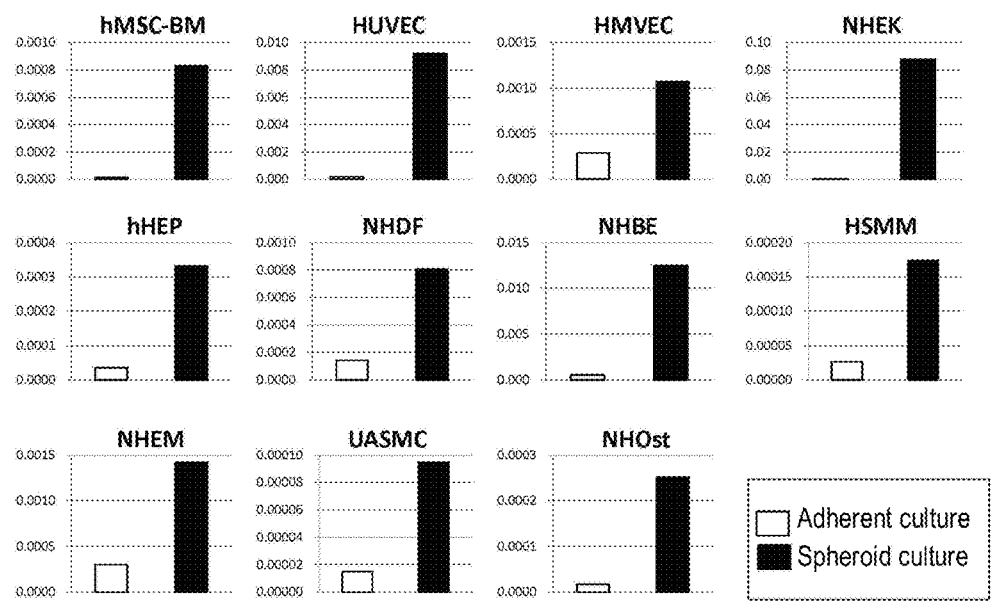

[Figure 15]
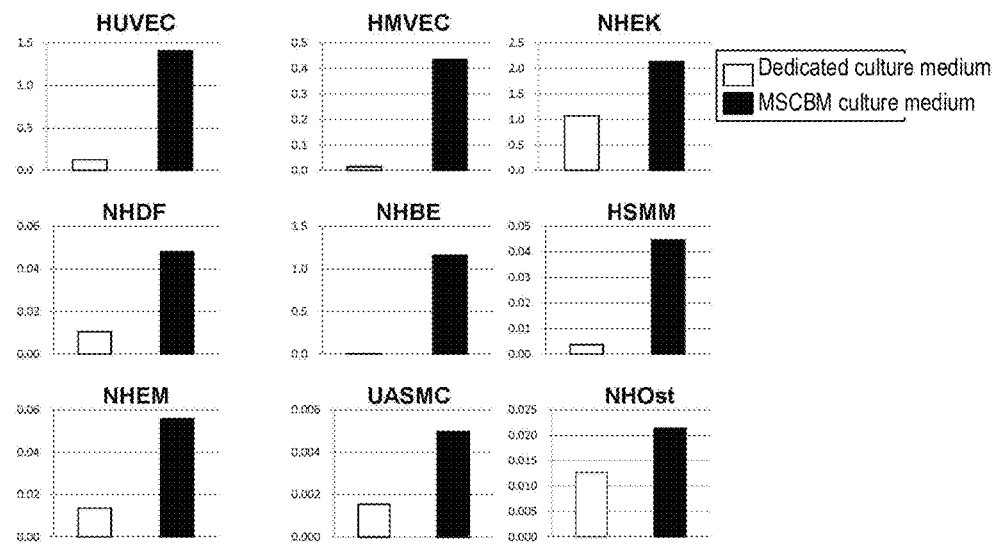

[Figure 16]
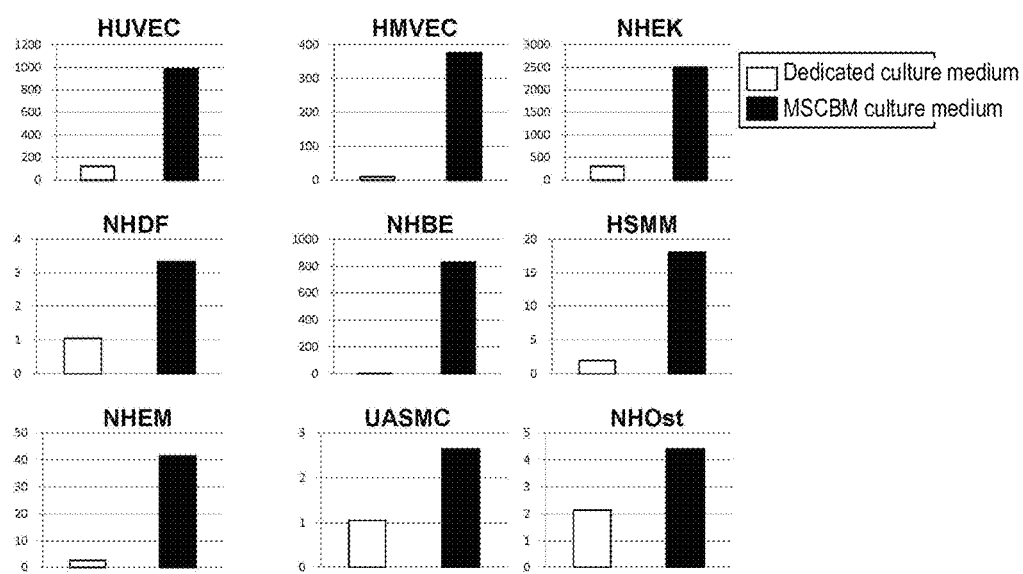

[Figure 17]
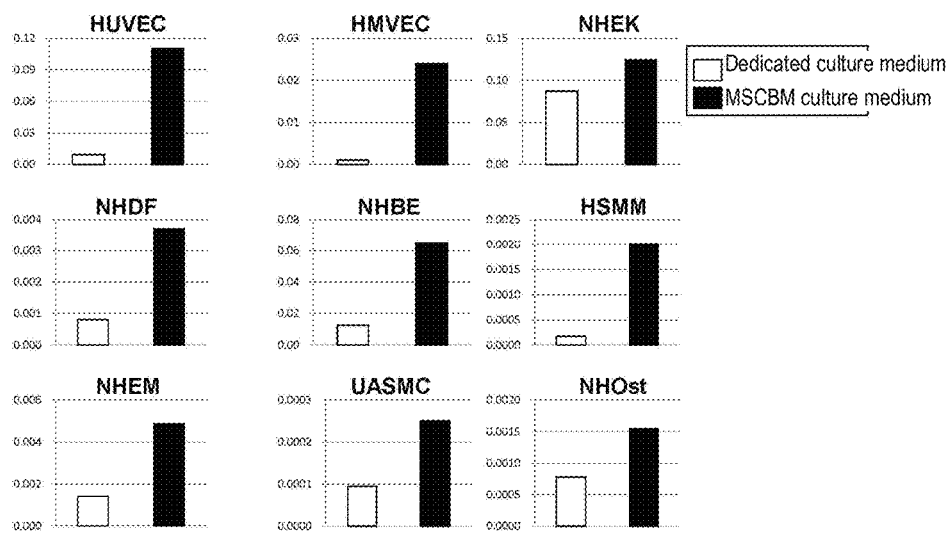
[Figure 18]
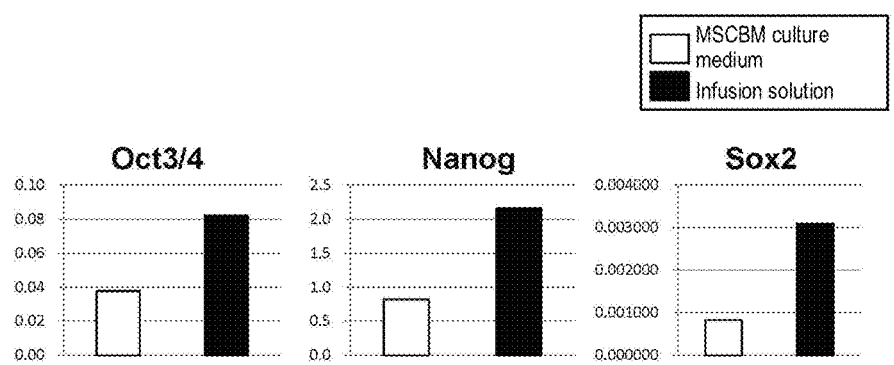

[Figure 19]
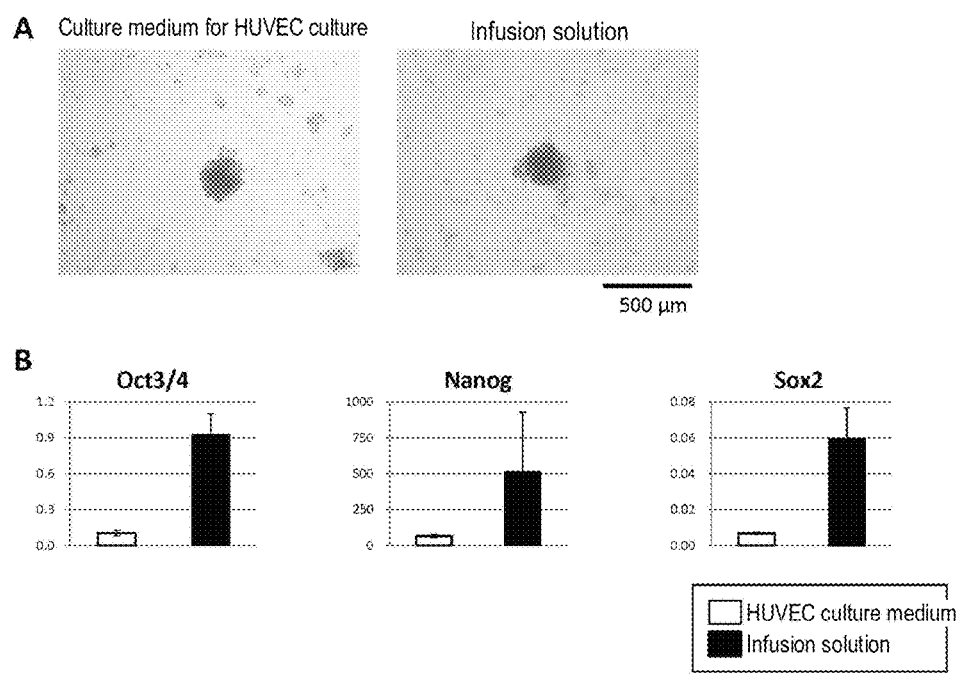

[Figure 20]
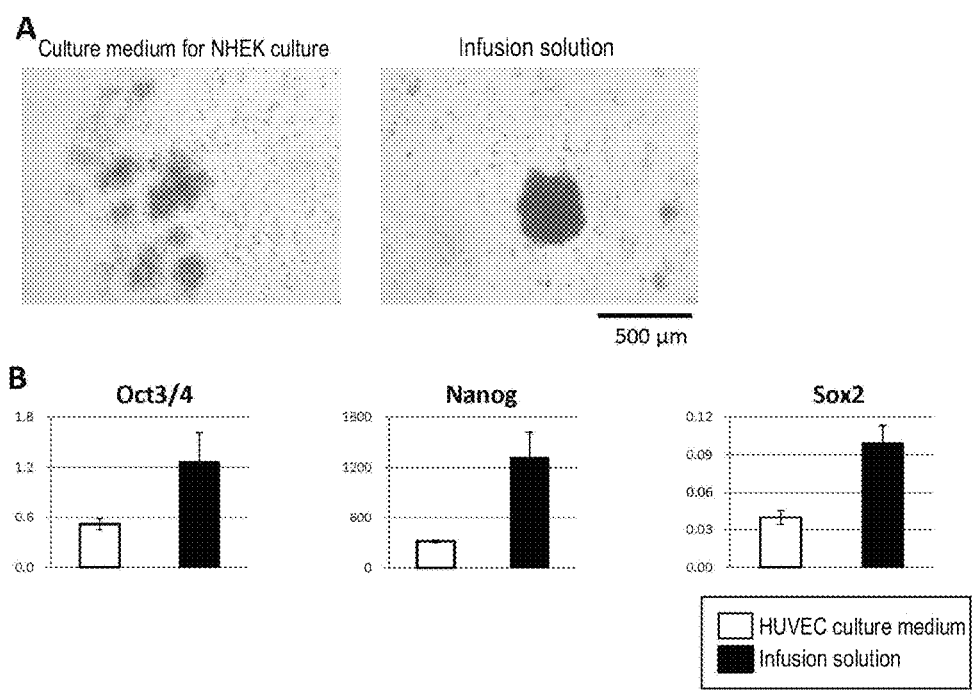

[Figure 21]
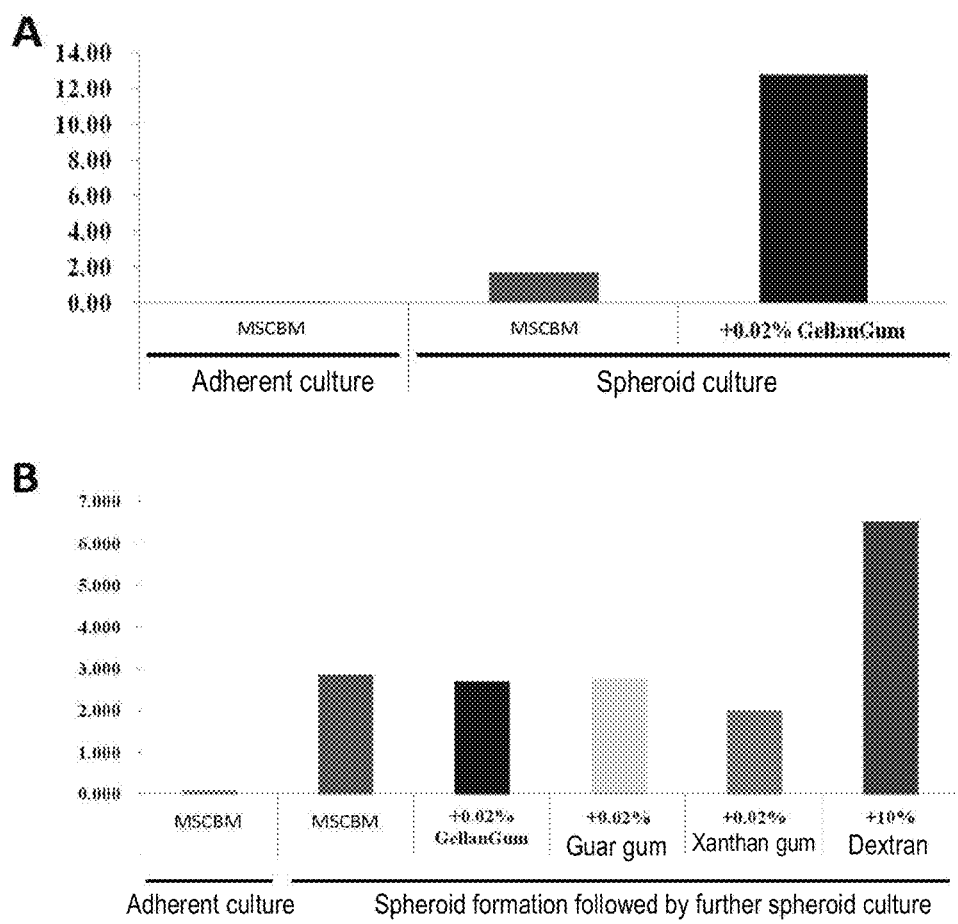

[Figure 22]
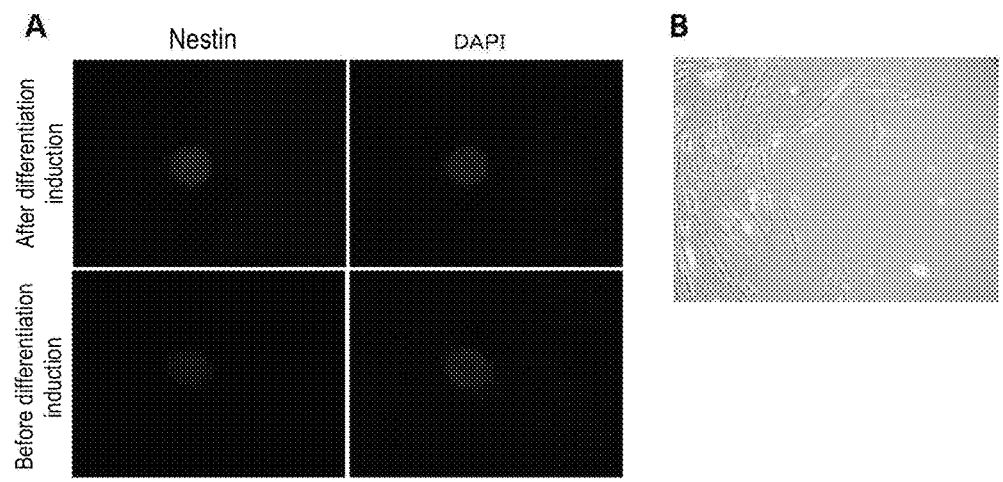
[Figure 23]
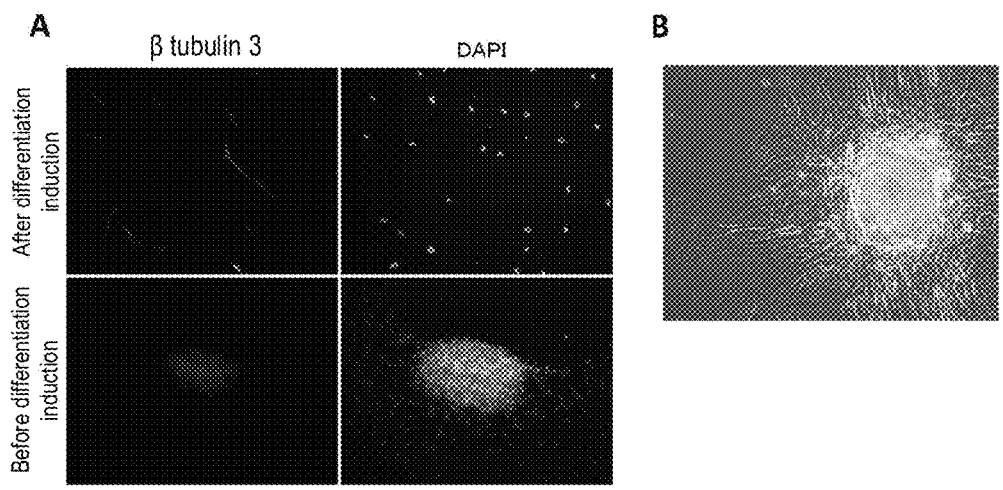

[Figure 24]
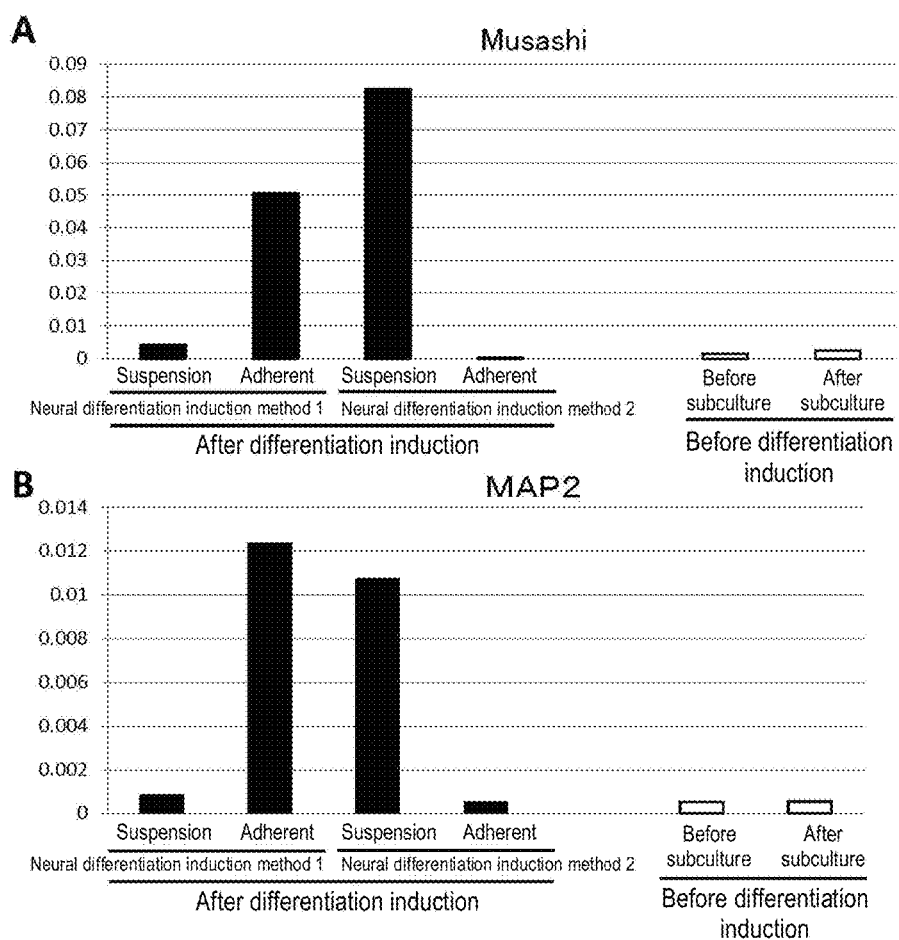

[Figure 25]
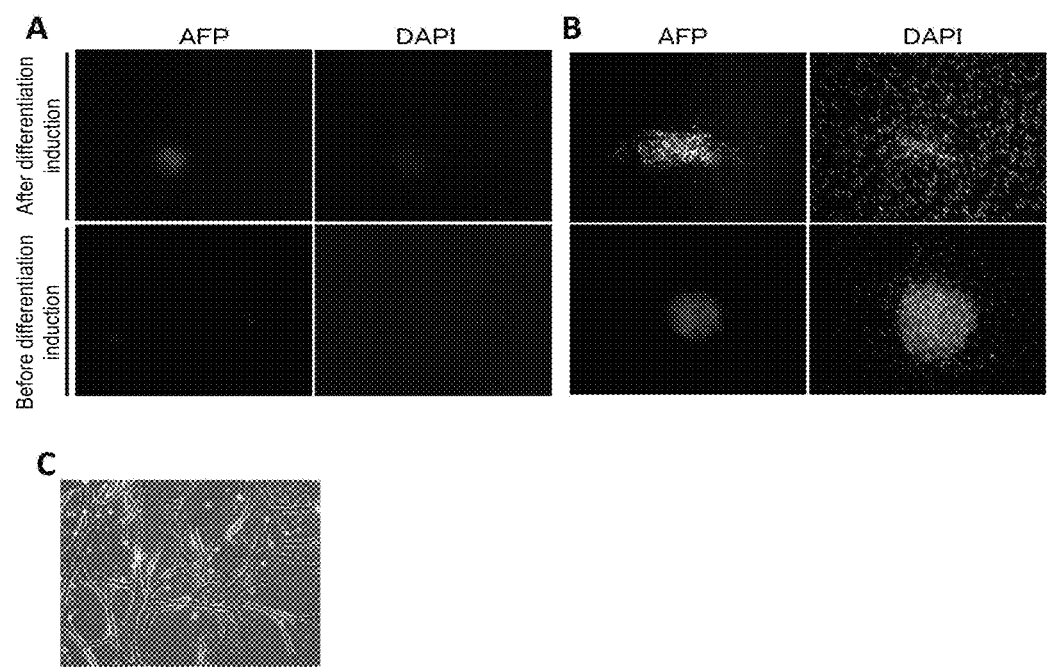

[Figure 26]
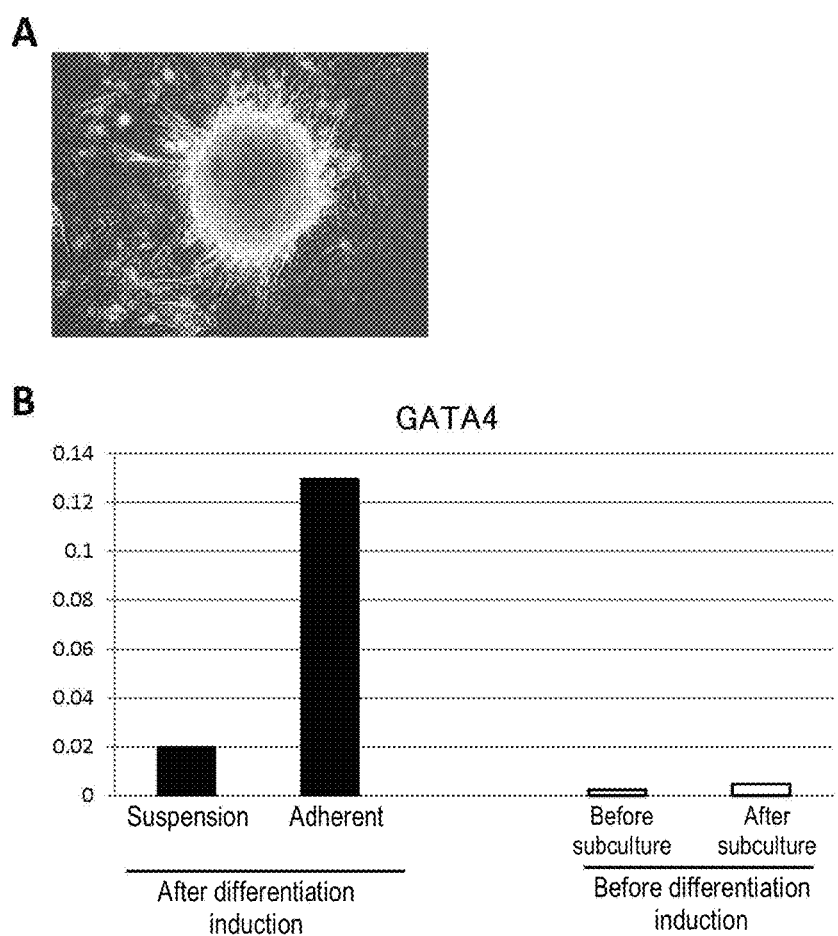

[Figure 27]
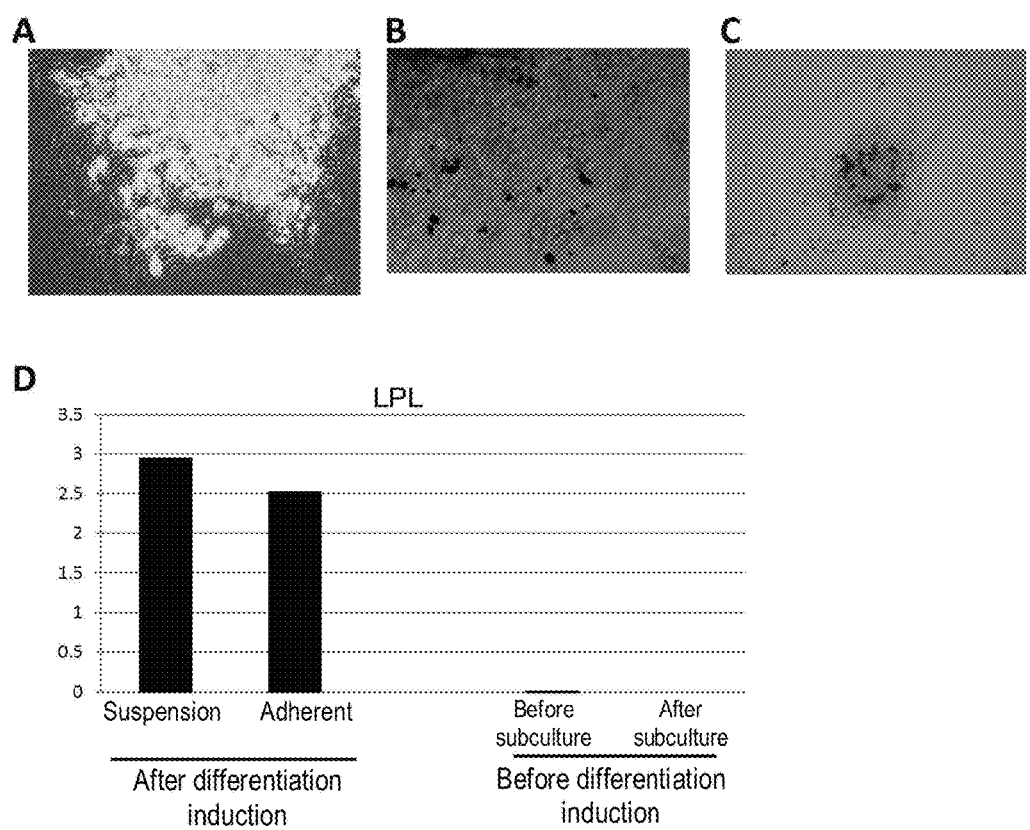

[Figure 28]
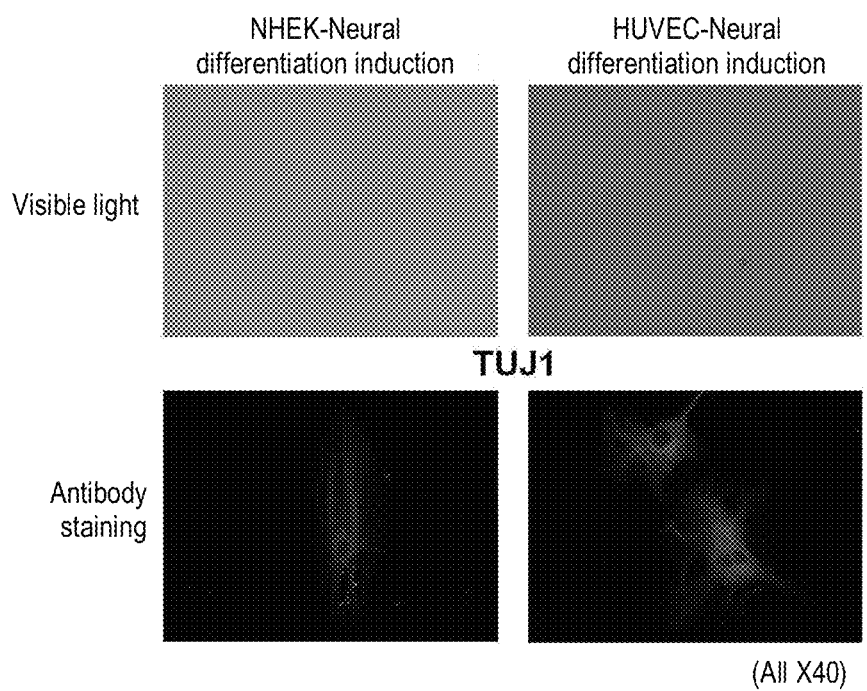

METHOD FOR PREPARING PLURIPOTENT STEM CELLS

TECHNICAL FIELD

The present invention relates to a method for preparing a pluripotent stem cell, comprising the step of suspension-culturing mammalian mesenchymal stem cells to form a cell mass of pluripotent stem cells, a pluripotent stem cell obtained by the preparation method, an agent for ameliorating decline in function or functional disorder of an organ or a tissue, comprising the pluripotent stem cell, a method for inducing differentiation of the pluripotent stem cell, etc.

BACKGROUND ART

Pluripotent stem cells are cells having the ability to differentiate into every cell present in the living body. Embryonic stem cells (ES cells) are a typical example thereof. Human ES cells are expected to be applied to regenerative medicine through the use of this property. The transplantation of differentiated ES cells, however, causes undesired rejection.

In recent years, the group of Yamanaka et al. has reported the development of so-called iPS cells (induced pluripotent stem cells), which are cells having pluripotency or a proliferative potential close to that of ES cells, by inducing dedifferentiation through the expression of 4 factors (Oct3/4, Sox2, Klf4, and c-myc) using mouse somatic cells (non-patent document 1), and then reported that the iPS cells can also be prepared from differentiated human cells (non-patent document 2). Such human iPS cells can be prepared using cells derived from patients to be treated and are therefore expected as tools for preparing artificial organs free from rejection. Nonetheless, the analysis of the in vivo behaviors of the iPS cells has suggested the possibility that the iPS cells are not necessarily cells having the same properties as those of ES cells. For example, as a result of preparing chimeric mice using iPS cells, tumor formation was observed in approximately 20% individuals. This is a significantly higher numeric value than that obtained in a similar experiment using ES cells.

To solve this problem of the high risk of tumor formation, it has been reported that: iPS cells can be prepared using only 3 factors (Oct3/4 gene, Sox2 gene, and Klf4 gene) without the use of c-myc known as an oncogene; and the risk of tumor formation can be reduced by the preparation of chimeric mice using the iPS cells (non-patent documents 3 and 4). However, the risk of tumor formation as close to zero as possible is required for the clinical application of pluripotent stem cells such as human iPS cells. Therefore, the risk of tumorigenic transformation is still viewed as a problem for the clinical application of iPS cells.

Meanwhile, studies are also ongoing to directly isolate pluripotent stem cells from living tissues. It has been reported that: a stress such as trypsin or hypoxic treatment can be applied to human bone marrow mesenchymal cells to thereby select stress-resistant pluripotent stem cells; and pluripotent stem cells can be selected with the expression of a pluripotent stem cell surface antigen SSEA-3 as an index and further isolated by repeated suspension culture (patent document 1 and non-patent document 5). These methods, however, require the operation of applying a stress to cells or selecting pluripotent stem cells with the expression of SSEA-3 as an index and are therefore susceptible to improvement in terms of time-effectiveness or cost-effectiveness.

PRIOR ART DOCUMENTS

Patent Documents

Patent Document 1: Japanese Patent No. 5185443

Non-patent Documents

Non-patent Document 1: Takahashi, K. et al., Cell. 126: 663-676 (2006)
Non-patent Document 2: Takahashi, K. et al., Cell. 131: 861-872 (2007)
Non-patent Document 3: Nakagawa, M. et al., Nat Biotechnol 26: 101-106 (2008)
Non-patent Document 4: Wering, M. et al., Cell Stem Cell 2: 10-12 (2008)
Non-patent Document 5: Kuroda, Y. et al., Proc Natl Acad Sci USA. 107: 8639-8643 (2010)

SUMMARY OF THE INVENTION

Object to be Solved by the Invention

An object of the present invention is to provide a method capable of inexpensively and conveniently preparing cells having pluripotency and a very low risk of tumorigenic transformation.

Means to Solve the Object

While conducting diligent studies to attain the object, the present inventors have suspension-cultured human mesenchymal stem cells from bone marrow (hMSC-BM) and human adipose tissue-derived mesenchymal stem cells (hAT-MSC) (also referred to as "human adipose-derived stem cells [hADSC]"), 7 types of human adherent mature cells (human hepatocyte cells [hHEP cells], human umbilical vein endothelial cells [HUVEC cells], human dermal lymphatic microvascular endothelial cells [HMVEC cells], human epidermal keratinocyte cells [NHEK cells], human bronchial epithelial cells [NHBE cells], human melanocyte cells [NHEM cells], and human smooth muscle cells [UASMC cells]), and 3 types of human adherent precursor cells (human dermal fibroblast cells [NHDF cells], human skeletal muscle myoblast cells [HSMM cells], and human osteoblast cells [NHOst cells]) to form cell masses (spheroids) and consequently found that pluripotent stem cells expressing a pluripotent stem cell marker protein can be induced (or isolated). The present inventors have also confirmed that the efficiency of pluripotency acquisition is enhanced by the spheroid culture of hMSC-BM cells in an infusion solution (serum-free culture medium) or a culture medium containing gellan gum or dextran. As a result of analyzing the prepared spheroid of hMSC-BM cells for its multilineage potential, the present inventors have also confirmed that the spheroid of hMSC-BM cells is cells having the ability to differentiate into cells derived from 3 embryos (ectoderm, endoderm, and mesoderm) (multilineage potential). The present inventors have further confirmed that the prepared spheroid of hMSC-BM cells or spheroid of hADSC cells is cells having a very low risk of tumorigenic transformation. The present invention has been completed on the basis of these findings.

Specifically, the present invention relates to (1) a method for preparing a pluripotent stem cell, comprising the step of suspension-culturing mammalian mesenchymal stem cells to form a cell mass of pluripotent stem cells (hereinafter, also referred to as the "present preparation method 1"), (2) the method according to (1), wherein the mammalian mesenchymal stem cells are human mesenchymal stem cells from bone marrow or human adipose tissue-derived mesenchymal stem cells, (3) the method according to (1) or (2), wherein the pluripotent stem cell expresses Nanog, Oct3/4, or Sox2, (4) the method according to any one of (1) to (3), wherein the suspension-culturing is performed in a solution containing (A) gellan gum or a derivative thereof or a salt of these; or (B) dextran or a derivative thereof or a salt of these, and (5) the method according to any one of (1) to (4), wherein the suspension-culturing is performed in a physiological aqueous solution free from serum or a serum substitute.

The present invention also relates to (6) a pluripotent stem cell obtainable by the method according to any one of (1) to (5).

The present invention also relates to (7) a pluripotent stem cell obtained by suspension-culturing mammalian mesenchymal stem cells, (8) the pluripotent stem cell according to (7), wherein the mammalian mesenchymal stem cells are human mesenchymal stem cells from bone marrow or human adipose tissue-derived mesenchymal stem cells, (9) the pluripotent stem cell according to (7) or (8), wherein the pluripotent stem cell expresses Nanog, Oct3/4, or Sox2, (10) the pluripotent stem cell according to any one of (7) to (9), wherein the suspension-culturing is performed in a solution containing (A) gellan gum or a derivative thereof or a salt of these; or (B) dextran or a derivative thereof or a salt of these, and (11) the pluripotent stem cell according to any one of (7) to (10), wherein the suspension-culturing is performed in a physiological aqueous solution free from serum or a serum substitute (hereinafter, the pluripotent stem cell of (6) to (11) is also referred to as the "present pluripotent stem cell 1").

The present invention also relates to (12) an agent for ameliorating decline in function or functional disorder of an organ or a tissue, comprising the pluripotent stem cell according to any one of (6) to (11) (hereinafter, also referred to as the "present ameliorating agent 1").

The present invention also relates to (13) a method for inducing differentiation of a pluripotent stem cell, comprising the step of subjecting a pluripotent stem cell obtained by the method according to any one of (1) to (5) to a differentiation treatment (hereinafter, also referred to as the "present differentiation induction method 1").

According to another embodiment, the present invention can relate to [1] a method for preparing a pluripotent stem cell, comprising the step of suspension-culturing mammalian adherent mature cells or mammalian adherent precursor cells to form a cell mass of pluripotent stem cells (hereinafter, also referred to as the "present preparation method 2"), [2] the method according to [1], wherein the pluripotent stem cell expresses Nanog, Oct3/4, or Sox2, [3] the method according to [1] or [2], wherein the suspension-culturing is performed in a solution containing (A) gellan gum or a derivative thereof or a salt of these; or (B) dextran or a derivative thereof or a salt of these, and [4] the method according to any one of [1] to [3], wherein the suspension-culturing is carried out in a physiological aqueous solution free from serum or a serum substitute.

According to an alternative embodiment, the present invention can relate to [5] a pluripotent stem cell obtainable by the method according to any one of [1] to [4].

According to an alternative embodiment, the present invention can relate to [6] a pluripotent stem cell obtained by suspension-culturing mammalian adherent mature cells or mammalian adherent precursor cells, [7] the pluripotent stem cell according to [6], wherein the pluripotent stem cell expresses Nanog, Oct3/4, or Sox2, [8] the pluripotent stem cell according to [6] or [7], wherein the suspension-culturing is performed in a solution containing (A) gellan gum or a derivative thereof or a salt of these; or (B) dextran or a derivative thereof or a salt of these, and [9] the pluripotent stem cell according to any one of [6] to [8], wherein the suspension-culturing is performed in a physiological aqueous solution free from serum or a serum substitute (hereinafter, the pluripotent stem cell of [5] to [9] is also referred to as the "present pluripotent stem cell 2").

According to an alternative embodiment, the present invention can relate to [10] an agent for ameliorating decline in function or functional disorder of an organ or a tissue, comprising the pluripotent stem cell according to any one of [5] to [9] (hereinafter, also referred to as the "present ameliorating agent 2").

According to an alternative embodiment, the present invention can relate to [11] a method for inducing differentiation of a pluripotent stem cell, comprising the step of subjecting a pluripotent stem cell prepared by the preparation method according to any one of [1] to [4] to differentiation treatment (hereinafter, also referred to as the "present differentiation induction method 2").

According to an alternative embodiment, the present invention can relate to a method for treating a patient having decline in function or functional disorder of an organ or a tissue, comprising administering the present pluripotent stem cell 1 or the present pluripotent stem cell 2 to the patient.

According to an alternative embodiment, the present invention can relate to use of a cell obtained by suspension-culturing mammalian mesenchymal stem cells as a pluripotent stem cell, and use of a cell obtained by suspension-culturing mammalian adherent mature cells or mammalian adherent precursor cells as a pluripotent stem cell.

According to an alternative embodiment, the present invention can relate to the present pluripotent stem cell 1 or the present pluripotent stem cell 2 for use as an agent for ameliorating (treating) decline in function or functional disorder of an organ or a tissue.

According to an alternative embodiment, the present invention can relate to use of the present pluripotent stem cell 1 or the present pluripotent stem cell 2 for the production of an agent for ameliorating (treating) decline in function or functional disorder of an organ or a tissue.

Effect of the Invention

Use of the present preparation method 1 and the present preparation method 2 can produce the present pluripotent stem cell 1 and the present pluripotent stem cell 2, i.e., cells having pluripotency and a very low risk of tumorigenic transformation. These cells are useful in the safe treatment of diseases such as heart failure, insulin-dependent diabetes mellitus, Parkinson's disease, and spinal cord injury. Moreover, the present pluripotent stem cell 1 and the present pluripotent stem cell 2 can be prepared by suspension culture and are therefore excellent because these cells can be prepared conveniently at a large scale in a relatively short time as compared with the preparation of iPS cells by gene transfer to cells.

BRIEF DESCRIPTION OF DRAWINGS

FIG. 1 is a diagram showing results of analyzing the expression of a pluripotent stem cell marker protein (Nanog) in adherent-cultured hMSC-BM cells (upper boxes) and spheroid-cultured hMSC-BM cells (lower boxes). The left diagrams show phase-contrast images, and the right diagrams show fluorescent images.

FIG. 2 is a diagram showing results of analyzing the expression of a pluripotent stem cell marker protein (Oct3/4) in adherent-cultured hMSC-BM cells (upper boxes) and spheroid-cultured hMSC-BM cells (lower boxes). The left diagrams show phase-contrast images, and the right diagrams show fluorescent images.

FIG. 3 is a diagram showing results of analyzing the expression of a pluripotent stem cell marker protein (Sox2) in adherent-cultured hMSC-BM cells (upper boxes) and spheroid-cultured hMSC-BM cells (lower boxes). The left diagrams show phase-contrast images, and the right diagrams show fluorescent images.

FIG. 4 is a diagram showing results of analyzing the expression of a pluripotent stem cell marker protein (SSEA3) in adherent-cultured hMSC-BM cells (upper boxes) and spheroid-cultured hMSC-BM cells (lower boxes). The left diagrams show phase-contrast images, and the right diagrams show fluorescent images.

FIG. 5 is a diagram showing results of analyzing the expression of mRNAs of 3 types of pluripotent stem cell marker genes (Nanog [upper left box], Oct3/4 [upper right box], and Sox2 [lower left box]) in adherent-cultured hMSC-BM cells and spheroid-cultured hMSC-BM cells.

FIG. 6 is a diagram showing results of analyzing the expression of a pluripotent stem cell marker protein (Nanog) in adherent-cultured hADSC cells (upper boxes) and spheroid-cultured hADSC cells (lower boxes). The left diagrams show phase-contrast images, and the right diagrams show fluorescent images.

FIG. 7 is a diagram showing results of analyzing the expression of a pluripotent stem cell marker protein (Oct3/4) in adherent-cultured hADSC cells (upper boxes) and spheroid-cultured hADSC cells (lower boxes). The left diagrams show phase-contrast images, and the right diagrams show fluorescent images.

FIG. 8 is a diagram showing results of analyzing the expression of a pluripotent stem cell marker protein (Sox2) in adherent-cultured hADSC cells (upper boxes) and spheroid-cultured hADSC cells (lower boxes). The left diagrams show phase-contrast images, and the right diagrams show fluorescent images.

FIG. 9 is a diagram showing results of analyzing the expression of a pluripotent stem cell marker protein (SSEA3) in adherent-cultured hADSC cells (upper boxes) and spheroid-cultured hADSC cells (lower boxes). The left diagrams show phase-contrast images, and the right diagrams show fluorescent images.

FIG. 10 is a diagram showing results of analyzing the expression of mRNAs of 3 types of pluripotent stem cell marker genes (Nanog [upper left box], Oct3/4 [upper right box], and Sox2 [lower left box]) in adherent-cultured hADSC cells and spheroid-cultured hADSC cells.

FIG. 11 is a diagram showing microscope images of spheroid-cultured cells (hMSC-BM and 7 types of adherent mature cells [HUVEC, HMVEC, NHEK, hHEP, NHBE, NHEM, and UASMC cells] and 3 types of adherent precursor cells [NHDF, HSMM, and NHOst cells]). The scale bar in the diagram represents 500 μm.

FIG. 12 is a diagram showing results of analyzing the expression of mRNA of a pluripotent stem cell marker gene (Oct3/4) in adherent-cultured cells (hMSC-BM and 7 types of adherent mature cells mentioned above and 3 types of adherent precursor cells mentioned above) and spheroid-cultured cells (hMSC-BM and 7 types of adherent mature cells mentioned above and 3 types of adherent precursor cells mentioned above).

FIG. 13 is a diagram showing results of analyzing the expression of mRNA of a pluripotent stem cell marker gene (Nanog) in adherent-cultured cells (hMSC-BM and 7 types of adherent mature cells mentioned above and 3 types of adherent precursor cells mentioned above) and spheroid-cultured cells (hMSC-BM and 7 types of adherent mature cells mentioned above and 3 types of adherent precursor cells mentioned above).

FIG. 14 is a diagram showing results of analyzing the expression of mRNA of a pluripotent stem cell marker gene (Sox2) in adherent-cultured cells (hMSC-BM and 7 types of adherent mature cells mentioned above and 3 types of adherent precursor cells mentioned above) and spheroid-cultured cells (hMSC-BM and 7 types of adherent mature cells mentioned above and 3 types of adherent precursor cells mentioned above).

FIG. 15 is a diagram showing results of analyzing the expression of mRNA of a pluripotent stem cell marker gene (Oct3/4) in 6 types of adherent mature cells (HUVEC, HMVEC, NHEK, NHBE, NHEM, and UASMC cells) and 3 types of adherent precursor cells (NHDF, HSMM, and NHOst cells), wherein these 6 types of adherent mature cells and 3 types of adherent precursor cells were spheroid-cultured in their respective dedicated culture media or spheroid-cultured in MSCBM culture media.

FIG. 16 is a diagram showing results of analyzing the expression of mRNA of a pluripotent stem cell marker gene (Nanog) in 6 types of adherent mature cells mentioned above and 3 types of adherent precursor cells mentioned above, wherein these 6 types of adherent mature cells and 3 types of adherent precursor cells were spheroid-cultured in their respective dedicated culture media or spheroid-cultured in MSCBM culture media.

FIG. 17 is a diagram showing results of analyzing the expression of mRNA of a pluripotent stem cell marker gene (Sox2) in 6 types of adherent mature cells mentioned above and 3 types of adherent precursor cells mentioned above, wherein these 6 types of adherent mature cells and 3 types of adherent precursor cells were spheroid-cultured in their respective dedicated culture media or spheroid-cultured in MSCBM culture media.

FIG. 18 is a diagram showing results of analyzing the expression of mRNAs of 3 types of pluripotent stem cell marker genes (Oct3/4, Nanog, and Sox2) in hMSC-BM cells spheroid-cultured in an MSCBM culture medium and hMSC-BM cells spheroid-cultured in an infusion solution.

FIG. 19A shows a phase-contrast image of HUVEC cells spheroid-cultured in a culture medium for HUVEC culture (left diagram), and a phase-contrast image of HUVEC cells spheroid-cultured in an infusion solution (right diagram). FIG. 19B is a diagram showing results of analyzing the expression of mRNAs of 3 types of pluripotent stem cell marker genes (Oct3/4, Nanog, and Sox2) in the HUVEC cells spheroid-cultured in a culture medium for HUVEC culture and the HUVEC cells spheroid-cultured in an infusion solution (mean±standard deviation, [n=3]).

FIG. 20A shows a phase-contrast image of NHEK cells spheroid-cultured in a culture medium for NHEK culture (left diagram), and a phase-contrast image of NHEK cells spheroid-cultured in an infusion solution (right diagram). FIG. 20B is a diagram showing results of analyzing the expression of mRNAs of 3 types of pluripotent stem cell marker genes (Oct3/4, Nanog, and Sox2) in the NHEK cells spheroid-cultured in a culture medium for NHEK culture and the NHEK cells spheroid-cultured in an infusion solution (mean±standard deviation, [n=3]).

FIG. 21A is a diagram showing results of analyzing the expression of mRNA of a pluripotent stem cell marker gene (Nanog) in hMSC-BM cells spheroid-cultured in a culture medium containing gellan gum. FIG. 21B is a diagram showing results of analyzing the expression of mRNA of the pluripotent stem cell marker gene (Nanog) in a spheroid of hMSC-BM cells further spheroid-cultured in a culture medium containing gellan gum, guar gum, xanthan gum, or dextran.

FIG. 22 is a diagram showing results of analyzing the expression of a neuronal cell marker protein (nestin) after differentiation induction treatment of a spheroid of hMSC-BM cells into neuronal cells (ectoderm-derived cells) by suspension culture using culture medium supplemented with CNTF (ciliary neurotrophic factor) (hereinafter, referred to as the "neural differentiation induction method 1") (see non-patent document 5 and Examples described herein) (FIG. 22A), and results of observing cell morphology under a microscope (FIG. 22B).

FIG. 23 is a diagram showing results of analyzing the expression of a neuronal cell marker protein (β tubulin 3) after differentiation induction treatment of a spheroid of hMSC-BM cells into neuronal cells by adherent culture using culture medium supplemented with Noggin (hereinafter, referred to as the "neural differentiation induction method 2") (see the document "Wada, et al., PLoS One. 4 (8): e6722 (2009)" and Examples described herein) (FIG. 23A), and results of observing cell morphology under a microscope (FIG. 23B).

FIG. 24 is a diagram showing results of analyzing the expression of mRNAs of 2 types of neural progenitor cell marker genes (Musashi [FIG. 24A] and MAP2 [FIG. 24B]) after differentiation induction treatment of a spheroid of hMSC-BM cells into neuronal cells.

FIGS. 25A and 25B are diagrams showing results of analyzing the expression of a liver cell marker protein (AFP) after differentiation induction treatment of a spheroid of hMSC-BM cells into liver cells (endoderm-derived cells) by suspension culture and adherent culture, respectively. FIG. 25C is a diagram showing results of observing cell morphology under a microscope after the differentiation induction treatment of the spheroid of hMSC-BM cells into liver cells by suspension culture.

FIG. 26A is a diagram showing results of observing cell morphology under a microscope after differentiation induction treatment of a spheroid of hMSC-BM cells into heart muscle cells (mesoderm-derived cells) by adherent culture. FIG. 26B is a diagram showing results of analyzing the expression of mRNA of a heart muscle cell marker gene (GATA4) after differentiation induction treatment of a spheroid of hMSC-BM cells into heart muscle cells by suspension culture or adherent culture.

FIG. 27A is a diagram showing results of observing cell morphology under a microscope after differentiation induction treatment of a spheroid of hMSC-BM cells into fat cells (mesoderm-derived cells) by adherent culture. FIGS. 27B and 27C are diagrams showing results of analyzing fat droplets by an oil red staining method after differentiation induction treatment of a spheroid of hMSC-BM cells into fat cells by suspension culture and adherent culture, respectively. FIG. 27D is a diagram showing results of analyzing the expression of mRNA of a fat cell marker gene (LPL) after the differentiation induction treatment of the spheroid of hMSC-BM cells into fat cells by suspension culture or adherent culture.

FIG. 28 The upper left box of FIG. 28 is a diagram showing results of observing cell morphology under a microscope after differentiation induction treatment of a spheroid of NHEK cells into neuronal cells. The upper right box of FIG. 28 is a diagram showing results of observing cell morphology under a microscope after differentiation induction treatment of a spheroid of HUVEC cells into neuronal cells. The lower left box of Figure is a diagram showing results of analyzing the expression of a neuronal cell marker protein (TUJ1) after the differentiation induction treatment of the spheroid of NHEK cells into neuronal cells. The lower right box of FIG. 28 is a diagram showing results of analyzing the expression of the neuronal cell marker protein (TUJ1) after the differentiation induction treatment of the spheroid of HUVEC cells into neuronal cells.

MODE OF CARRYING OUT THE INVENTION

The present pluripotent stem cell 1 is a cell that forms a cell mass (spheroid) (hereinafter, also referred to as the "present pluripotent stem cell mass 1") obtained by suspension-culturing mammalian mesenchymal stem cells, and is usually used as a pluripotent stem cell. Also, the present pluripotent stem cell 2 is a cell that forms a cell mass (spheroid) (hereinafter, also referred to as the "present pluripotent stem cell mass 2") obtained by suspension-culturing mammalian adherent mature cells or mammalian adherent precursor cells, and is usually used as a pluripotent stem cell. In the present invention, the phrase "used as a pluripotent stem cell" means use (transplantation) for the purpose of imparting paracrine effects to in vivo cells as well as use (transplantation) for the purpose of differentiating into cells derived from 3 germ layers (ectoderm, endoderm, and mesoderm) in vivo, and use of for differentiating into the cells of interest derived from these 3 germ layers in vitro. In the present invention, the cell for use as a pluripotent stem cell means a cell limited by its use, i.e., "for use as a pluripotent stem cell".

Examples of the mammal of the present invention can include: a rodent such as a mice, a rat, a hamster, and a guinea pig; an animal of the order Lagomorpha such as a rabbit; an animal of the order Ungulata such as a pig, cattle, a goat, a horse, and sheep; an animal of the order Carnivora such as a dog and a cat; and a primate such as a human, a monkey, a rhesus monkey, a cynomolgus monkey, a marmoset, an orangutan, and a chimpanzee. Among them, a mouse, a pig, or a human is preferred. In the case of using the present pluripotent stem cell 1 or the present pluripotent stem cell 2 in regenerative medicine, particularly preferred examples of the mammal can include a human.

The present pluripotent stem cell 1 or the present pluripotent stem cell 2 is a cell that cannot become an individual by itself, but has the ability to differentiate into every tissue or cell constituting the living body and has no or a very low risk of tumorigenic transformation when transplanted to a mammal. The present pluripotent stem cell 1 or the present pluripotent stem cell 2 differs from pluripotent stem cells such as embryonic stem cells (ES cells), embryonic germ cells (EG cells), germline stem cells (GS cells), and iPS cells (induced pluripotent stem cell), which have a high risk of tumorigenic transformation when transplanted to a mammal, multipotent stem cells having the ability to differentiate into plural types of tissues or cells, albeit not all types, or unipotent stem cells (precursor cells) having the ability to differentiate into a particular tissue or cells.

In the present invention, the "suspension culture" means culture under conditions where cells or a cell mass (spheroid), i.e., a cell clump having a three-dimensional structure (spherical or aciniform shape) formed by an assembly of a large number of cells, does not adhere to an incubator (spheroid culture).

In the present specification, the "adherent mature cells" mean anchorage-dependent cells that can survive, grow, and produce matter by adhering to the anchorage and have already been differentiated (completely differentiated). The adherent mature cells have the property of stably maintaining the differentiated state without dedifferentiation under usual culture conditions. Specifically, the adherent mature cells include mature cells such as heart muscle cells, vascular endothelial cells, neuronal cells, fat cells, dermal fibrocyte cells, skeletal muscle cells, bone cells, hepatocyte (liver) cells, umbilical vein endothelial cells, dermal lymphatic microvascular endothelial cells, epidermal keratinocyte cells, bronchial epithelial cells, melanocyte cells, smooth muscle cells, and dentinal cells, but exclude stem cells including pluripotent stem cells such as ES cells, EG cells, GS cells, and iPS cells, multipotent stem cells such as mesenchymal stem cells, hematopoietic stem cells, and neural stem cells, and unipotent stem cells (precursor cells) such as cardiac progenitor cells, vascular endothelial progenitor cells, neural progenitor cells, preadipocyte cells, dermal fibroblast cells, skeletal muscle myoblast cells, osteoblast cells, and odontoblast cells, and floating cells such as red blood cells and white blood cells (neutrophils, monocytes, lymphocytes, macrophages, etc.).

In the present specification, the "adherent precursor cells" mean anchorage-dependent cells that can survive, grow, and produce matter by adhering to the anchorage and differentiate into a particular tissue or cells. Specifically, the adherent precursor cells include the unipotent stem cells (precursor cells) mentioned above, but exclude the pluripotent stem cells, the multipotent stem cells, the mature cells, and the floating cells.

The present pluripotent stem cell 1 and the present pluripotent stem cell 2 have pluripotency (multilineage potential) and are more characterized by the expression of a pluripotency marker such as Nanog, Oct3/4, Sox2, SSEA3, or TRA-1-60. Mammalian mesenchymal stem cells, when usually cultured (adherent-cultured), express no pluripotency marker. Therefore, the expression level of the pluripotency marker in the present pluripotent stem cell 1 or the present pluripotent stem cell 2 is increased compared with the expression level of the pluripotency marker in usually cultured mammalian mesenchymal stem cells (hereinafter, referred to as the "expression level of the control"). For example, the expression level of mRNA of the Nanog gene in the present pluripotent stem cell 1 is increased by usually 2 or more times, preferably 8 or more times, more preferably 20 or more times, further preferably 30 or more times, still further preferably 50 or more times, compared with the expression level of the control. The expression level of mRNA of the Oct3/4 gene in the present pluripotent stem cell 1 is increased by usually 2 or more times, preferably 3 or more times, more preferably 4 or more times, further preferably 4.5 or more times, still further preferably 5 or more times, particularly preferably 5.5 or more times, most preferably 6 or more times, compared with the expression level of the control. The expression level of mRNA of the Sox2 gene in the present pluripotent stem cell 1 is increased by usually 2 or more times, preferably 3 or more times, more preferably 4 or more times, further preferably 4.5 or more times, still further preferably 5 or more times, particularly preferably 5.5 or more times, most preferably 6 or more times, compared with the expression level of the control. The expression level of mRNA of the Nanog gene in the present pluripotent stem cell 2 is increased by usually 2 or more times, preferably 3 or more times, more preferably 9 or more times, further preferably 15 or more times, still further preferably 20 or more times, particularly preferably 100 or more times, most preferably 1000 or more times, compared with the expression level of the control. The expression level of mRNA of the Oct3/4 gene in the present pluripotent stem cell 2 is increased by usually 1.5 or more times, preferably 2 or more times, more preferably 3 or more times, further preferably 4 or more times, still further preferably 10 or more times, particularly preferably 50 or more times, most preferably 1000 or more times, compared with the expression level of the control. The expression level of mRNA of the Sox2 gene in the present pluripotent stem cell 2 is increased by usually 1.5 or more times, preferably 2 or more times, more preferably 3 or more times, further preferably 4 or more times, still further preferably 10 or more times, particularly preferably 50 or more times, most preferably 1000 or more times, compared with the expression level of the control.

The mammalian mesenchymal stem cells of the present invention are not particularly limited as long as the stem cells are derived from the bone marrow, the periosteum, peripheral blood, umbilical cord blood, or an adipose tissue and are capable of differentiating into a tissue of the mesenchymal tissue system (adipose tissue, cartilage tissue, bone tissue, etc.). Mammalian mesenchymal stem cells from bone marrow are preferred because the cells are easy to collect from living tissues and a culture method after collection has been established. Also, adipose tissue-derived mesenchymal stem cells are preferred because the cells are easy to collect as an excess tissue from the living body and are low invasive when collected.

The present ameliorating agent 1 and the present ameliorating agent 2 comprise the present pluripotent stem cell 1 and the present pluripotent stem cell 2, respectively, i.e., cells having pluripotency and a very low risk of tumorigenic transformation, as an active ingredient and have the effect of ameliorating (treating) decline in function or functional disorder of an organ or a tissue.

Examples of the organ or the tissue can include the brain, the lung, the liver, the kidney, the heart, the bowel (large intestine, small intestine, colon, etc.), the pancreas, bone (bone marrow), and the skin, etc.

Specific examples of the decline in function or the functional disorder of an organ or a tissue can include heart failure, insulin-dependent diabetes mellitus, Parkinson's disease, spinal cord injury, and dermatitis.

The number of the present pluripotent stem cell 1 or the present pluripotent stem cell 2 contained in the present ameliorating agent 1 or the present ameliorating agent 2 differs depending on a disease site to receive a transplant or the level of decline in function or the level of functional disorder of the organ or the tissue and also differs between local administration and systemic administration. Therefore, the number of the present pluripotent stem cell 1 or the present pluripotent stem cell 2 cannot be generalized and is usually $1 \times 10$ to $1 \times 10^{11}$ cells.

Examples of the method for administering the present ameliorating agent 1 or the present ameliorating agent 2 to a patient having the decline in function or the functional disorder of an organ or a tissue can include a method such as catheterization, injection into the coronary artery or vein or directly into the organ or the tissue responsible for the disease, and injection into the vein.

The mammalian mesenchymal stem cells from bone marrow used in the present preparation method 1 can be collected from a long bone such as humerus, costa, thigh bone, or tibia, a short bone such as carpus or tarsus, or a flat bone such as calvaria, scapula, or pelvis (ilium) where the bone marrow is present. The mammalian mesenchymal stem cells from bone marrow are preferably collected from thigh bone, tibia, or pelvis (ilium) because the cells can be collected in a large amount and are easy to collect.

The mammalian adipose tissue-derived mesenchymal stem cells used in the present preparation method 1 can be collected from a subcutaneous tissue or a visceral tissue where the adipose tissue is present. The mammalian adipose tissue-derived mesenchymal stem cells are preferably collected from a subcutaneous tissue because the cells can be collected in a large amount and are easy to collect.

The mammalian mesenchymal stem cells collected by a standard method from the living tissue can be isolated by adherent culture according to a method that abides by a primary culture method.

The mammalian adherent mature cells or the mammalian adherent precursor cells can be collected by a standard method from an organ or a tissue such as the skin (epidermis, dermis, subcutaneous tissue, etc.), muscle, heart muscle, nerve, bone, cartilage, blood vessel, the brain, the heart, the kidney, the liver, the pancreas, the spleen, oral cavity, cornea, bone marrow, umbilical cord blood, amnion, or hair and isolated by adherent culture according to a method that abides by a primary culture method.

In the present preparation method 1 or the present preparation method 2, the mammalian mesenchymal stem cells, the mammalian adherent mature cells, or the mammalian adherent precursor cells are usually adherent-cultured in a culture medium for animal cell culture (DMEM, EMEM, RPMI-1640, α-MEM, F-12, F-10, M-199, etc.) containing 0.1 to 30% (v/v) serum (fetal bovine serum [FBS], calf bovine serum [CS], etc.) and may be adherent-cultured in a culture medium optimized according to the properties (characteristics) of the cells. Specific examples of such a culture medium can include a culture medium (an MSCBM culture medium, an ADSC-BM culture medium, a culture medium for hHEP culture, a culture medium for HUVEC culture, a culture medium for HMVEC culture, a culture medium for NHEK culture, a culture medium for NHDF culture, a culture medium for NHBE culture, a culture medium for HSMM culture, a culture medium for NHEM culture, a culture medium for UASMC culture, and a culture medium for NHOst culture) used in Examples described herein or Reference Examples described herein.

The adherent culture can be carried out using an incubator such as a glass or plastic multiwall plate, a culture plate (Petri dish or dish), or a flask. In this context, the plastic incubator includes an incubator surface-treated with a hydrophilic polymer such as polyacrylamide, polydimethylacrylamide, polyacrylic acid or a salt thereof, polyhydroxyethyl methacrylate, polyhydroxyethyl acrylate, polyvinyl alcohol, polyvinylpyrrolidone, cellulose, or carboxymethylcellulose, or a cell adhesion molecule such as fibronectin, vitronectin, laminin, nidogen, tenascin, thrombospondin, fibrinogen, collagen, hyaluronic acid, gelatin, poly-L-lysine, or poly-D-lysine such that the cells easily adhere thereto. The incubator surface-treated with a hydrophilic polymer or a cell adhesion molecule may be commercially available or may be self-prepared. Examples of the commercially available product of the incubator surface-treated with a hydrophilic polymer can include Cell Culture Flask (manufactured by TPP Techno Plastic Products AG), Petri Dish (manufactured by TPP Techno Plastic Products AG), and Culture Ware for Primalia (manufactured by Nippon Becton Dickinson Co., Ltd.). Examples of the commercially available product of the incubator surface-treated with a cell adhesion molecule can include BD Biocoat Laminin-Coated Product (manufactured by Nippon Becton Dickinson Co., Ltd.), Biocoat Poly-D-lysine/Laminin Dish (manufactured by Cosmo Bio Co., Ltd.), Biocoat Poly-L-ornithine/Laminin Plate (manufactured by Cosmo Bio Co., Ltd.), and Biocoat Laminin/Fibronectin Plate (manufactured by Cosmo Bio Co., Ltd.). Examples of the commercially available product of the glass incubator can include Chamber Slide II (manufactured by Iwaki/AGC Techno Glass Co., Ltd.), BD Falcon Culture Slide (manufactured by Nippon Becton Dickinson Co., Ltd.), and Chamber Slide (manufactured by Matsunami Glass Ind., Ltd.). The mammalian mesenchymal stem cells have the property of adhering to an incubator for growth and can therefore be separated from hematopoietic stem cells, which float during growth.

The adherent culture can be carried out under conditions suitable for the culture of the mammalian mesenchymal stem cells, the mammalian adherent mature cells, or the mammalian adherent precursor cells. The culture temperature applied to this culture is usually in the range of approximately 30 to 40° C., preferably 37° C. The $CO_2$ concentration during the culture is usually in the range of approximately 1 to 10%, preferably approximately 5%. The humidity during the culture is usually in the range of approximately 70 to 100%, preferably approximately 95 to 100%. If necessary, the culture medium may be replaced.

The isolation of the mammalian mesenchymal stem cells can be confirmed using, as an index, the detected expression of a marker protein (positive marker), such as CD106, CD166, CD29, CD105, CD73, CD44, CD90, or CD71, which is expressed in mesenchymal stem cells, or the non-detected expression of a marker protein (negative marker), such as CD31, CD18, CD56, CD45, CD34, CD14, CD11, CD80, CD86, or CD40, which is not expressed in mesenchymal stem cells. The isolated mammalian mesenchymal stem cells can be cryopreserved by use of a method routinely used.

The suspension culture of the mammalian mesenchymal stem cells, the mammalian adherent mature cells, or the mammalian adherent precursor cells can be carried out by suspension-culturing the cells on a low adhesive incubator surface-coated with, for example, polyhydroxyethyl methacrylic acid (poly-HEMA), hydrogel, or MPC polymer (2-methacryloylethyl phosphoryl choline), or a non-adhesive incubator uncoated with the cell adhesion molecule.

The low adhesive incubator or the non-adhesive incubator may be commercially available or may be self-prepared. Examples of the commercially available low adhesive incubator can include a commercially available product such as EZSPHERE (vessel for spheroid formation culture) (manufactured by Iwaki/AGC Techno Glass Co., Ltd.), NCP (NanoCulture Plate) (manufactured by SCIVAX Life Sciences, Inc.), and ULA (Ultra-Low Adhesive surface) culture vessel (manufactured by Corning Inc.). Examples of the commercially available non-adhesive incubator can include a commercially available product such as Petri Dish for suspension culture (manufactured by Nunc/Thermo Fisher Scientific, Inc.), Petri Dishes for suspension cell culture (manufactured by Sumitomo Bakelite Co., Ltd.), and Non-Treatment Plate (manufactured by BD Falcon/Nippon Becton Dickinson Co., Ltd.).

The suspension culture is carried out in a solution in which the mammalian mesenchymal stem cells, the mammalian adherent mature cells, or the mammalian adherent precursor cells can form a cell mass of the present pluripotent stem cell 1 or the present pluripotent stem cell 2. Examples of such a solution can include: a culture medium containing serum or a serum substitute (serum replacement component), such as a culture medium for animal cell culture (DMEM, EMEM, RPMI-1640, α-MEM, F-12, F-10, M-199, etc.) containing 0.1 to 30% (v/v) serum (FBS, CS, etc.), the aforementioned culture medium for animal cell culture supplemented with an appropriate amount (e.g., 1 to 30%) of a serum substitute, and a culture medium used in Examples described herein or Reference Examples described herein (an MSCBM culture medium, an ADSC-BM culture medium, a culture medium for hHEP culture, a culture medium for HUVEC culture, a culture medium for HMVEC culture, a culture medium for NHEK culture, a culture medium for NHDF culture, a culture medium for NHBE culture, a culture medium for HSMM culture, a culture medium for NHEM culture, a culture medium for UASMC culture, a culture medium for NHOst culture, and a culture medium for hMSC culture); and a physiological aqueous solution free from serum or a serum substitute (serum replacement component), such as saline, saline having a buffering effect (phosphate buffered saline [PBS], Tris buffered saline [TBS], HEPES buffered saline, etc.), a Ringer's solution (lactate Ringer's solution, acetate Ringer's solution, bicarbonate Ringer's solution, etc.), a 5% aqueous glucose solution, the aforementioned culture medium for animal cell culture, an isotonic agent (glucose, D-sorbitol, D-mannitol, lactose, sodium chloride, etc.), and an infusion solution used in Examples described herein. A physiological aqueous solution free from serum or a serum substitute (serum replacement component) is preferred. Specific examples thereof can include an infusion solution used in Examples described herein. The supplementation with gellan gum or dextran enhances the efficiency of pluripotency acquisition. Therefore, the aforementioned solution containing any one or both of gellan gum or a derivative thereof or a salt of the material or the derivative (hereinafter, also referred to as "gellan gum, etc.") and dextran or a derivative thereof or a salt of the material or the derivative (hereinafter, also referred to as "dextran, etc.") is preferred.

Since the suspension culture of the cell mass of the present pluripotent stem cell 1 or the present pluripotent stem cell 2 in the presence of dextran enhances the efficiency of pluripotency acquisition, the present preparation method 1 or the present preparation method 2 preferably further comprises the step of suspension-culturing the cell mass of the present pluripotent stem cell 1 or the present pluripotent stem cell 2 in the aforementioned solution containing dextran, etc., after the step of forming the cell mass of the present pluripotent stem cell 1 or the present pluripotent stem cell 2.

The gellan gum in the gellan gum, etc. is not particularly limited as long as the gellan gum is a linear heteropolysaccharide constituted by repeat units derived from 4 sugars, i.e., glucose, glucuronic acid, glucose, and rhamnose. Examples thereof can include deacylated-type gellan gum and native-type gellan gum. Kelcogel® or the like is commercially available as the deacylated-type gellan gum. Kelcogel® LT100, Kelcogel® HM, Kelcogel® HT, or the like is commercially available as the native-type gellan gum. In the present invention, the deacylated-type gellan gum is preferred.

The gellan gum derivative in the gellan gum, etc. can be any product obtained by subjecting the gellan gum to a standard chemical reaction such as esterification or addition of a salt of an organic or inorganic acid. Specific examples thereof can include welan gum.

Examples of the salt of the gellan gum or the derivative in the gellan gum, etc. can include: an acid-addition salt such as hydrochloride, hydrobromide, hydroiodide, phosphate, nitrate, sulfate, acetate, propionate, toluenesulfonate, succinate, oxalate, lactate, tartrate, glycolate, methanesulfonate, butyrate, valerate, citrate, fumarate, maleate, and malate; a metal salt such as sodium salt, potassium salt, and calcium salt; an ammonium salt; and an alkyl ammonium salt. These salts are each used in the form of a solution upon application and preferably have effects equivalent to those of the gellan gum. These salts may each form a hydrate or a solvate. Any one of these salts can be used alone, or two or more thereof can be used in appropriate combination.

The concentration of the gellan gum, etc. in the aforementioned solution is usually in the range of 0.001 to 1.0% (w/v), preferably 0.005 to 0.2% (w/v), more preferably 0.01 to 0.2% (w/v).

The dextran in the dextran, etc. is not particularly limited as long as the dextran is a polysaccharide $(C_6H_{10}O_5)_n$ composed of D-glucose units and has an α1→6 bond in the principal chain. Examples of the weight-average molecular weight (Mw) of the dextran can include dextran (Mw=40000) and dextran 70 (Mw=70000). These dextrans can be produced by any method known in the art such as chemical synthesis, microbial production, or enzymatic production. Alternatively, a commercially available product can also be used. Examples thereof can include a commercially available product such as Low Molecular Dextran L Injection (manufactured by Otsuka Pharmaceutical Factory, Inc.) and Dextran 70 (manufactured by Tokyo Chemical Industry Co., Ltd.).

Examples of the dextran derivative in the dextran, etc. can include dextran sulfate, carboxylated dextran, and diethylaminoethyl (DEAE)-dextran.

Examples of the salt of the dextran or the derivative in the dextran, etc. can include: an acid-addition salt such as hydrochloride, hydrobromide, hydroiodide, phosphate, nitrate, sulfate, acetate, propionate, toluenesulfonate, succinate, oxalate, lactate, tartrate, glycolate, methanesulfonate, butyrate, valerate, citrate, fumarate, maleate, and malate; a metal salt such as sodium salt, potassium salt, and calcium salt; an ammonium salt; and an alkyl ammonium salt. These salts are each used in the form of a solution upon application and preferably have effects equivalent to those of the dextran. These salts may each form a hydrate or a solvate. Any one of these salts can be used alone, or two or more thereof can be used in appropriate combination.

The concentration of the dextran, etc. in the aforementioned solution is usually 0.1% (w/v) or higher, preferably 0.5% (w/v) or higher, more preferably 1.0% (w/v) or higher. Also, the concentration of the dextran, etc. in the aforementioned solution is, for example, 20% (w/v) or lower, preferably 15% (w/v) or lower, more preferably 12% (w/v) or lower, further preferably 10% (w/v) or lower, from the viewpoint of circumventing adverse effects on the survival rate of the cells. Thus, the concentration of the dextran, etc. in the aforementioned solution is, for example, 0.1 to 20% (w/v), preferably 0.5 to 15% (w/v), more preferably 1.0 to 12% (w/v), further preferably 1.0 to 10% (w/v).

The culture medium containing serum or a serum substitute or the physiological aqueous solution free from serum or a serum substitute may be supplemented, if necessary, with an appropriate additive such as a stabilizer (e.g., human serum albumin and polyethylene glycol), a buffer (e.g., a phosphate buffer solution and a sodium acetate buffer solution), a chelating agent (e.g., EDTA, EGTA, citric acid, and salicylate), an amino acid (e.g., a nonessential amino acid such as glutamine, alanine, asparagine, serine, aspartic acid, cysteine, glutamic acid, glycine, proline, and tyrosine), a vitamin (e.g., choline chloride, pantothenic acid, folic acid, nicotinamide, pyridoxal hydrochloride, riboflavin, thiamin hydrochloride, ascorbic acid, biotin, and inositol), a polysaccharide (e.g., guar gum and xanthan gum), a solubilizing agent, a preservative, or an antioxidant.

In the present invention, the "serum substitute" means a material (component) that is used instead of serum for cell culture or growth and has effects similar to those of serum. Specific examples of the serum substitute can include commercially available B27 Supplement (without insulin) (manufactured by Life Technologies, Inc.), N2 Supplement (manufactured by Life Technologies, Inc.), B27 Supplement (manufactured by Life Technologies, Inc.), and Knockout Serum Replacement (manufactured by Invitrogen Corp.).

The culture conditions for carrying out the suspension culture can be appropriately selected within culture conditions (temperature, time, cell density, etc.) under which a spheroid of the present pluripotent stem cell 1 or the present pluripotent stem cell 2 can be formed. For example, the cell density at the start of the suspension culture is usually $1 \times 10$ to $1 \times 10^8$ cells, preferably $1 \times 10^2$ to $1 \times 10^6$ cells, more preferably $1 \times 10^3$ to $1 \times 10^5$ cells. The culture temperature applied to the culture is usually in the range of approximately 30 to 40° C., preferably 37° C. The $CO_2$ concentration during the culture is usually in the range of approximately 1 to 10%, preferably approximately 5%. The humidity during the culture is usually in the range of approximately 70 to 100%, preferably approximately 95 to 100%. If necessary, the culture medium may be replaced. The culture time can be any period during which the present pluripotent stem cell 1 or the present pluripotent stem cell 2 can be prepared at a sufficient rate. The culture time is usually 5 hours to 4 weeks, preferably 1 day to 3 weeks, more preferably 3 days to 2 weeks.

The pluripotency of the cell prepared by the present preparation method 1 or the present preparation method 2 can be confirmed using the detected expression of a pluripotency marker such as Nanog, Oct3/4, Sox2, SSEA3, or TRA-1-60 as an index. Examples of the method for detecting the expression of the pluripotency marker can include: a method which involves extracting or purifying total RNA from the cell, followed by detection by Northern blotting using a probe consisting of a nucleotide sequence complementary to mRNA of the pluripotency marker gene; a method which involves extracting or purifying total RNA from the cell, and synthesizing cDNA using reverse transcriptase, followed by detection by quantitative PCR (e.g., competitive PCR and real-time PCR) using a primer pair specifically amplifying the cDNA derived from mRNA of the pluripotency marker gene; a method which involves purifying total RNA from the cell, synthesizing cDNA using reverse transcriptase, then labeling the cDNA with biotin, digoxigenin, or the like, and indirectly labeling the cDNA with a fluorescent material-labeled avidin having high affinity for biotin or a fluorescent material-labeled antibody recognizing digoxigenin, followed by detection using a microarray in which a probe consisting of a nucleotide sequence complementary to the cDNA of the pluripotency marker gene is immobilized on a support available in hybridization, such as a glass, silicon, or plastic support; and immunoassay using an antibody specifically recognizing the pluripotency marker protein (immunohistochemical staining, ELISA, EIA, RIA, Western blotting, etc.).

In the case of preparing a cell suspension of the present pluripotent stem cell 1 or the present pluripotent stem cell 2 having high purity in the present preparation method 1 or the present preparation method 2, the cell suspension is prepared from the cell mass of the present pluripotent stem cell 1 or the present pluripotent stem cell 2 using a cell-dispersing solution (trypsin, lysyl endopeptidase, pronase, pepsin, elastase, collagenase, hyaluronidase, etc.), a pipette, or Pipetman and subjected to isolation treatment with a fluorescence activated cell sorter (FACS) using an antibody against a pluripotent stem cell surface marker (TRA-1-60, SSEA-3, etc.) or an automatic magnetic cell separation apparatus (autoMACS) using a conjugate antibody of a labeling material (fluorescent material, biotin, avidin, etc.)-labeled antibody against the pluripotent stem cell surface marker, an antibody against the labeling material, and MACS beads (magnetic beads). Examples of the fluorescent material can include allophycocyanin (APC), phycoerythrin (PE), FITC (fluorescein isothiocyanate), Alexa Fluor 488, Alexa Fluor 647, Alexa Fluor 700, PE-Texas Red, PE-Cy5, and PE-Cy7.

The present differentiation induction method 1 or the present differentiation induction method 2 is not particularly limited as long as the method comprises the step of subjecting the present pluripotent stem cell 1 or the present pluripotent stem cell 2 prepared using the present preparation method 1 or the present preparation method 2 to differentiation treatment. For enhancing the efficiency of differentiation, the method preferably further comprises, before the differentiation treatment of the prepared cell mass (present pluripotent stem cell mass 1 or present pluripotent stem cell mass 2), the step of treating the cell mass with the aforementioned cell-dispersing solution or suspending the cell mass of pluripotent stem cells in a single-cell state, and the step of suspension-culturing the single cells to form a cell mass. The solution or the culture conditions for suspension-culturing the single cells are as mentioned above. In the present specification, the "single-cell state" means that each individual cell does not form a clump together with other cells (i.e., a non-aggregated state). The proportion of cells in a single-cell state included in the pluripotent stem cells is usually 70% or more, preferably 90% or more, more preferably 95% or more, further preferably 99% or more, particularly preferably 100%. The proportion of cells in a single-cell state can be confirmed by observing the pluripotent stem cells in the suspension under a microscope and the presence or absence of aggregation as to a plurality of cells (e.g., 1000 cells) randomly selected.

The differentiation treatment can be appropriately carried out by use of a differentiation induction method for arbitrary cells with reference to a differentiation treatment method reported about pluripotent stem cells such as ES cells, iPS cells, or embryoid body (EB) cells. For example, the differentiation induction into neural stem cells can be carried out according to a method described in the document (Japanese unexamined Patent Application Publication No. 2002-291469) and can be carried out by the neural differentiation induction method (see non-patent document 5 and Examples described herein) or the neural differentiation induction method 2 (see the document "Wada, et al., PLoS One. 4 (8): e6722 (2009)" and Examples described herein).

The differentiation induction into pancreatic stem-like cells can be carried out according to a method described in the document (Japanese unexamined Patent Application Publication No. 2004-121165). The differentiation induction into hematopoietic cells can be carried out according to a method described in the documents (Japanese unexamined patent application Publication (Translation of PCT Application) No. 2003-505006 and International Publication No. WO 99/064565). The differentiation induction into muscle cells can be carried out according to a method described in the document (Boheler K. R, et al., Circ. Res. 91, 189-201, 2002). The differentiation induction into liver cells can be carried out by suspension culture or adherent culture using a culture medium supplemented with HGF (hepatocyte growth factor) (see Examples described herein). The differentiation induction into heart muscle cells can be carried out according to a method described in the documents (Klug M. G, et al., J. Clin. Invest. 98, 216-224, 1996; and Muller M, et al., FASEB. J. 14, 2540-2548, 2000). The differentiation induction into vascular endothelial cells or vascular smooth muscle cells can be carried out according to a method described in the documents (Vittet D, et al., Proc. Natl. Acad. Sci. USA 94, 6273-6278, 1997; Bloch W, et al., J. Cell Biol. 139, 265-278, 1997; Yamashita J, et al., Nature 408, 92-96, 2000; and Feraud O, et al., Lab. Invest. 81, 1669-1681, 2001). The differentiation induction into fat cells can be carried out by suspension culture or adherent culture using a culture medium for fat cell induction (manufactured by Lonza Group Ltd., PT-3004) (see Examples described herein). The differentiation induction into retinal cells can be carried out according to a method described in the documents (Ikeda H, et al., Proc. Natl. Acad. Sci. USA 102, 11331-11336, 2005; Osakada F, et al., Nat. Biotechnol. 26, 215-224, 2008; Osakada F, et al., Nat. Protoc. 4, 811-824, 2009; Hirami Y, et al., Neurosci. Lett. 458, 126-131, 2009; and Osakada F, et al., J Cell Sci 122, 3169-3179, 2009). The differentiation induction into dendritic cells can be carried out according to a method described in the document (Senju S, Haruta M, Matsunaga Y, et al., Stem Cells 27, 1021-1031, 2009).

Hereinafter, the present invention will be described more specifically with reference to Examples. However, the technical scope of the present invention is not intended to be limited by these examples.

Example 1

1. Confirmation that Cells Expressing Pluripotent Stem Cell Marker are Obtained by Spheroid Culture of hMSC-BM Cells
1-1 Method
1-1-1 Culture of hMSC-BM Cells and Spheroid Culture Method
[1] 16 mL of MSCBM (Mesenchymal Stem Cell Basal Medium) (manufactured by Lonza Group Ltd., PT-3238) supplemented with a set of supplements and factors for mesenchymal stem cells (manufactured by Lonza Group Ltd., PT-4105) (hereinafter, referred to as an "MSCBM culture medium") was added to a 75 cm² flask, and the culture medium was warmed and equilibrated in an incubator (37° C., 5% $CO_2$) (30 minutes or longer).
[2] hMSC-BM cells (manufactured by Lonza Group Ltd.) were taken out of liquid nitrogen and quickly thawed in a hot water bath of 37° C.
[3] The thawed cells were transferred to a 15 mL centrifuge tube preliminarily containing 5 mL of an MSCBM culture medium, and mixed.
[4] Centrifugation treatment was carried out at 500 g at 22° C. for 5 minutes.
[5] After removal of the supernatant, 1 mL of an MSCBM culture medium was added to the cells, which were then suspended by pipetting.
[6] 9 mL of an MSCBM culture medium was further added thereto, and the mixture was stirred.
[7] The number of cells was counted, and the cells were inoculated to a 75 cm² flask ($4.0 \times 10^5$ cells/flask).
[8] The cells were cultured in an incubator (37° C., 5% $CO_2$).
[9] The culture medium was replaced every 3 days or 4 days.
[10] After the cells became approximately 80% confluent, the culture medium was aspirated using an aspirator, and the cells were washed by the addition of 10 mL of PBS.
[11] After removal of PBS, approximately 3.75 mL of trypsin/EDTA (manufactured by Lonza Group Ltd.) was added to the cells. While the state of the cells was confirmed under a microscope, trypsin treatment was carried out at room temperature for 5 minutes. Then, the trypsin treatment was further carried out for 3 to 10 minutes when 90% or less of the cells were not dissociated.
[12] The trypsin treatment was terminated by the addition of an MSCBM culture medium of room temperature in an amount equal to that of trypsin/EDTA, and then, the cells were dissociated by pipetting and recovered into a 15 mL tube.
[13] Centrifugation treatment was carried out at 600 g at room temperature for 5 minutes.
[14] After removal of the supernatant, 1 mL of an MSCBM culture medium was added to the cells, which were then suspended by pipetting.
[15] 9 mL of an MSCBM culture medium was further added thereto, and the mixture was stirred.
[16] The number of cells was counted, and the cells were inoculated to a 75 cm₂ flask (3.75 to $4.5 \times 10^5$ cells/flask).
[17] The cells were cultured in an incubator (37° C., 5% $CO_2$).
[18] The culture medium was replaced every 3 days or 4 days.
[19] The steps [10] to [18] were repeated until the adequate number of cells (0.3 to $1 \times 10^8$ cells) for use in analysis was obtained.
[20] After the cells became approximately 80% confluent, the culture medium was aspirated using an aspirator, and the cells were washed by the addition of 10 mL of PBS.
[21] After removal of PBS, approximately 3.75 mL of trypsin/EDTA (manufactured by Lonza Group Ltd.) was added to the cells. While the state of the cells was confirmed under a microscope, trypsin treatment was carried out at room temperature for 5 minutes. Then, the trypsin treatment was further carried out for 3 to 10 minutes when 90% or less of the cells were not dissociated.
[22] The trypsin treatment was terminated by the addition of an MSCBM culture medium of room temperature in an amount equal to that of trypsin/EDTA, and then, the cells were dissociated by pipetting and recovered into a 15 mL tube.
[23] Centrifugation treatment was carried out at 600 g at room temperature for 5 minutes.
[24] After removal of the supernatant, 1 mL of an MSCBM culture medium was added to the cells, which were then suspended by pipetting.
[25] 9 mL of an MSCBM culture medium was further added thereto, and the mixture was stirred.
[26] The number of cells was counted, and the cells were inoculated to a low adhesive 100 mm dish (manufactured by Corning Inc.) and a 96-well plate (manufactured by Corning Inc.) ($1.0 \times 10^6$ cells/dish and $1.0 \times 10^4$ cells/plate) and spheroid-cultured for 7 days in an incubator (37° C., 5% $CO_2$).

1-1-2 Immunofluorescent Staining Method

[1] The hMSC-BM cells spheroid-cultured in a 96-well plate according to the method described in "1-1-1 Culture of hMSC-BM cells and spheroid culture method" were recovered into a 1.5 mL tube. hMSC-BM cells adherent-cultured in Chamber Slide (manufactured by Iwaki/AGC Techno Glass Co., Ltd.) were similarly subjected to the following procedures as a control without being dissociated.

[2] The spheroid-cultured cell mass was left standing until sinking to the bottom of the tube.

[3] After removal of the supernatant, the fixation treatment of the cells was carried out (15 minutes, room temperature) by the addition of 0.5 to 1 mL of 4% formaldehyde/PBS.

[4] The spheroid-cultured cell mass was left standing until sinking to the bottom of the tube.

[5] After removal of the supernatant, the washing treatment of the cells was carried out (5 minutes, room temperature) by the addition of 1 to 1.5 mL of PBS.

[6] The spheroid-cultured cell mass was left standing until sinking to the bottom of the tube.

[7] The steps [5] and [6] were repeated twice.

[8] After removal of the supernatant, the permeabilization treatment of the cells was carried out (5 minutes, room temperature) by the addition of 0.5 to 1 mL of Triton/PBS.

[9] The spheroid-cultured cell mass was left standing until sinking to the bottom of the tube.

[10] After removal of the supernatant, the washing treatment of the cells was carried out (5 minutes, room temperature) by the addition of 1 to 1.5 mL of PBS.

[11] The spheroid-cultured cell mass was left standing until sinking to the bottom of the tube.

[12] The steps [10] and [11] were repeated once.

[13] After removal of the supernatant, the blocking treatment of the cells was carried out (1 to 2 hours, room temperature) by the addition of 1 mL of a blocking solution (5% normal serum/PBS or 3% BSA/PBS).

[14] The spheroid-cultured cell mass was left standing until sinking to the bottom of the tube.

[15] After removal of the supernatant, the primary antibody reaction treatment of the cells was carried out (overnight, 4° C.) by the addition of 0.5 to 1 mL of a primary antibody solution (anti-Nanog antibody [manufactured by Cell Signaling Technology, Inc., #4903S, diluted 1/800-fold], anti-Oct4 antibody [manufactured by Cell Signaling Technology, Inc., #2750S, diluted 1/400-fold], anti-Sox2 antibody [manufactured by Cell Signaling Technology, Inc., #3579S, diluted 1/400-fold], or anti-SSEA3 antibody [manufactured by EMD Millipore, A488, diluted 1/200-fold]) in order to detect the expression of 4 types of pluripotent stem cell marker proteins (Nanog, Oct3/4, Sox2, and SSEA3).

[16] After removal of the supernatant, the washing treatment of the cells was carried out (5 minutes, room temperature) by the addition of 1 to 1.5 mL of PBS.

[17] The spheroid-cultured cell mass was left standing until sinking to the bottom of the tube.

[18] The steps [16] and [17] were repeated twice.

[19] After removal of the supernatant, the secondary antibody reaction treatment of the cells was carried out (1 to 2 hours, room temperature) by the addition of 0.5 to 1 mL of a secondary antibody solution (Alexa Fluor 488 anti-rabbit antibody [manufactured by Invitrogen Corp., A21206, diluted 1/1000-fold], Alexa Fluor 555 anti-rabbit antibody [manufactured by Invitrogen Corp., A21428, diluted 1/1000-fold], or Alexa Fluor 488 anti-mouse antibody [manufactured by Invitrogen Corp., A21202, diluted 1/1000-fold]).

[20] After removal of the supernatant, the washing treatment of the cells was carried out (5 minutes, room temperature) by the addition of 1 to 1.5 mL of PBS.

[21] The spheroid-cultured cell mass was left standing until sinking to the bottom of the tube.

[22] The steps [20] and [21] were repeated twice.

[23] After removal of the supernatant, 1 to 1.5 mL of PBS was added to the cell mass, and the cell mass was left standing on a glass slide, or the top of Chamber Slide for adherent culture was removed. Then, Fluoromount (manufactured by Diagnostic BioSystems Inc.) was added dropwise thereto, and a glass cover was placed for enclosure to prepare cell samples for immunofluorescent staining.

[24] The fluorescent images and phase-contrast images of the cell samples were obtained using Axio Observer (manufactured by Carl Zeiss AG). Axio Vision (manufactured by Carl Zeiss AG) was used as analysis software.

1-1-3 mRNA Expression Analysis

[1] The hMSC-BM cells spheroid-cultured in a 100 mm dish according to the method described in "1-1-1 Culture of hMSC-BM cells and spheroid culture method" were recovered into a 15 mL centrifuge tube. Adherent-cultured hMSC-BM cells were recovered as a control and similarly subjected to the following procedures.

[2] Total RNA was extracted from the cells using RNeasy Mini Kit (manufactured by Qiagen N.V.) and QIA shredder (manufactured by Qiagen N.V.) according to the protocols attached to the products.

[3] The concentration of the extracted total RNA was measured using NanoDrop 2000 (manufactured by Thermo Fisher Scientific, Inc.).

[4] The total RNA was adjusted to 20 μg/mL and dispensed at 3 μL/well to a 96-well plate (Fast 96 well Reaction plate [manufactured by Applied Biosystems, Inc., #4309169]).

[5] A reaction solution consisting of 1) to 6) given below was prepared using TaqMan One-Step RT-PCR Master Mix Reagents Kit (manufactured by Applied Biosystems, Inc., #4309169) and added dropwise to the total RNA-dispensed 96-well plate in order to detect the expression level of mRNAs of 3 types of pluripotent stem cell marker genes (Nanog, Oct3/4, and Sox2) by RT-PCR. GAPDH gene was used as an internal standard.

1) Rnase-free water; 0.5 μL
2) 2x Master Mix without UNG; 10 μL (1x)
3) 40x MultiScribe and RNase Inhibitor Mix; 0.5 μL
4) Forward Primer; 2.0 μL (300 nM)
5) Reverse Primer; 2.0 μL (900 nM)
6) TaqMan Probe; 2.0 μL (200 nM)

Table 1 shows the nucleotide sequences of the primer sets (aforementioned "Forward Primer" and "Reverse Primer") for amplifying cDNAs of the 3 types of pluripotent stem cell marker genes and the nucleotide sequences of the probes (aforementioned "TaqMan Probe") hybridizing to the amplification (PCR) products.

| Primer or probe name | | Nucleotide sequence |
|---|---|---|
| Human Nanog (NM_024865.2) | | |
| Nanog | [Forward Primer] | 5'-TGGTCTCGATCTCC TGACCTT-3' (SEQ ID NO: 1) |

-continued

| Primer or probe name | | Nucleotide sequence |
|---|---|---|
| Nanog | [Reverse Primer] | 5'-GGCTCACGCCTGTA AATCC 3' (SEQ ID NO: 2) |
| Nanog | [TaqMan Probe] | 5'-TGATCCACCCGCCT CGGCCT-3' (SEQ ID NO: 3) |
| Human Oct3/4 (NM_002701) | | |
| Oct3/4 | [Forward Primer] | 5'-AACCCACACTGCAG CAGATC-3' (SEQ ID NO: 4) |
| Oct3/4 | [Reverse Primer] | 5'-CACACTCGGACCAC ATCCTT-3' (SEQ ID NO: 5) |
| Oct3/4 | [TaqMan Probe] | 5'-CCACATCGCCCAGC AGCTTGG-3' (SEQ ID NO: 6) |
| Human Sox2 (NM_003106) | | |
| Sox2 | [Forward Primer] | 5'-GCGCAGATGCAGCC CA-3' (SEQ ID NO: 7) |
| Sox2 | [Reverse Primer] | 5'-TCATGTAGGTCTGC GAGCTGG-3' (SEQ ID NO: 8) |
| Sox2 | [TaqMan Probe] | 5'-CACCGCTACGACGT GAGCGCCCT-3' (SEQ ID NO: 9) |
| Human GAPDH (NM_002046) | | |
| GAPDH | [Forward Primer] | 5'-CATGGGTGTGAACC ATGAGAA-3' (SEQ ID NO: 10) |
| GAPDH | [Reverse Primer] | 5'-GGTCATGAGTCCTT CCACGAT-3' (SEQ ID NO: 11) |
| GAPDH | [TaqMan Probe] | 5'-AACAGCCTCAAGAT CATCAGCAATGCCT-3' (SEQ ID NO: 12) |

[6] The mixed solution of the total RNA and the reaction solution prepared in the step [5] was used to carry out real-time RT-PCR with ABI PRISM 7000 Sequence Detection system (manufactured by Applied Biosystems, Inc.) under conditions shown below in 1) to 3).
1) 1 cycle of 48° C. for 30 minutes (reverse transcription reaction of mRNA to cDNA)
2) 1 cycle of 95° C. for 10 minutes (polymerase activation)
3) 40 round-trip cycles of 95° C. for 15 seconds and 60° C. for 1 minute (cDNA amplification with "Forward Primer" and "Reverse Primer")
[7] The number of PCR cycles at which the amount of the PCR product crosses the threshold level (threshold cycle; Ct value) was measured using Baseline software (manufactured by Applied Biosystems, Inc.). The relative Ct values of the cDNA amplification products of the 3 types of pluripotent stem cell marker genes with respect to the Ct value of the cDNA amplification product of the GAPDH gene were determined by the comparative Ct method (delta delta Ct method). From these relative Ct values, the relative cDNA levels of the 3 types of pluripotent stem cell marker genes, i.e., the relative mRNA levels of the 3 types of pluripotent stem cell marker genes, were calculated (see the ordinates of FIGS. 5 and 10).

1-2 Results

As a result of detecting the expression of 4 types of pluripotent stem cell marker proteins (Nanog, Oct3/4, Sox2, and SSEA3) using the immunofluorescent staining method, the expression of the 4 types of pluripotent stem cell marker proteins was not detected in the control adherent-cultured hMSC-BM cells, whereas the 4 types of pluripotent stem cell marker proteins were detected in the spheroid-cultured hMSC-BM cells (see FIGS. 1 to 4).

As a result of detecting and quantifying the mRNA expression levels of 3 types of pluripotent stem cell marker genes (Nanog, Oct3/4, and Sox2) by use of RT-PCR, the mRNA expression levels of Nanog and Oct3/4 were drastically increased by 57.8 times and 43.3 times, respectively, in the spheroid-cultured hMSC-BM cells compared with the control adherent-cultured hMSC-BM cells (see FIG. 5). Also, the mRNA expression level of Sox2 was not detected in the control adherent-cultured hMSC-BM cells, but was detected in the spheroid-cultured hMSC-BM cells (see FIG. 5). These results indicate that the spheroid culture of the hMSC-BM cells can induce (or isolate) cells expressing a pluripotent stem cell marker.

Example 2

2. Confirmation that Cells Expressing Pluripotent Stem Cell Marker are Obtained by Spheroid Culture of hADSC Cells 2-1 Method 2-1-1 Culture of hADSC Cells and Spheroid Culture Method

[1] 15 mL of ADSC-BM (Adipose Derived Stem Cell Basal Medium) (manufactured by Lonza Group Ltd., PT-3273) supplemented with a set of supplements and factors for human adipose-derived stem cells (manufactured by Lonza Group Ltd., PT-4503) (hereinafter, referred to as an "ADSC-BM culture medium") was added to a 75 cm$^2$ flask, and the culture medium was warmed and equilibrated in an incubator (37° C., 5% $CO_2$), (20 to 30 minutes or longer).
[2] hADSC cells (manufactured by Lonza Group Ltd.) were taken out of liquid nitrogen and quickly thawed in a hot water bath of 37° C.
[3] The thawed cells were transferred to a 15 mL centrifuge tube preliminarily containing 5 mL of an ADSC-BM culture medium, and mixed.
[4] Centrifugation treatment was carried out at 210 g at 22° C. for 5 minutes.
[5] After removal of the supernatant, 1 mL of an ADSC-BM culture medium was added to the cells, which were then suspended by pipetting.
[6] 9 mL of an ADSC-BM culture medium was further added thereto, and the mixture was stirred.
[7] The number of cells was counted, and the cells were inoculated to a 75 cm$^2$ flask ($3.75 \times 10^5$ cells/flask).
[8] The cells were cultured in an incubator (37° C., 5% $CO_2$).
[9] The culture medium was replaced every 3 days or 4 days.
[10] After the cells became approximately 90% confluent, the culture medium was aspirated using an aspirator, and the cells were washed by the addition of 5 mL of a HEPES buffer (manufactured by Lonza Group Ltd.).
[11] After removal of the HEPES buffer, approximately 3.75 mL of trypsin/EDTA (manufactured by Lonza Group Ltd.) was added to the cells. While the state of the cells was confirmed under a microscope, trypsin treatment was carried out at 37° C. for 3 to 5 minutes. Then, the trypsin treatment was further carried out for 2 minutes when 90% or less of the cells were not dissociated.

[12] The trypsin treatment was terminated by the addition of TNS (Trypsin Neutralization Solution) (manufactured by Lonza Group Ltd.) of room temperature in an amount of 2 times the amount of trypsin/EDTA, and then, the cells were dissociated by pipetting and recovered into a 15 mL tube.

[13] Centrifugation treatment was carried out at 210 g at room temperature for 5 minutes.

[14] After removal of the supernatant, 1 mL of an ADSC-BM culture medium was added to the cells, which were then suspended by pipetting.

[15] 9 mL of an ADSC-BM culture medium was further added thereto, and the mixture was stirred.

[16] The number of cells was counted, and the cells were inoculated to a 75 cm$_2$ flask (3.75 to 4.5×10$^5$ cells/flask).

[17] The cells were cultured in an incubator (37° C., 5% CO$_2$).

[18] The culture medium was replaced every 3 days or 4 days.

[19] The steps [10] to [18] were repeated until the adequate number of cells (0.3 to 1×10$^8$ cells) for use in analysis was obtained.

[20] After the cells became approximately 90% confluent, the culture medium was aspirated using an aspirator, and the cells were washed by the addition of 10 mL of PBS.

[21] After removal of PBS, approximately 3.75 mL of trypsin/EDTA (manufactured by Lonza Group Ltd.) was added to the cells. While the state of the cells was confirmed under a microscope, trypsin treatment was carried out at 37° C. for 3 to 5 minutes. Then, the trypsin treatment was further carried out for 2 minutes when 90% or less of the cells were not dissociated.

[22] The trypsin treatment was terminated by the addition of TNS (manufactured by Lonza Group Ltd.) of room temperature in an amount of 2 times the amount of trypsin/EDTA, and then, the cells were dissociated by pipetting and recovered into a 15 mL tube.

[23] Centrifugation treatment was carried out at 210 g at room temperature for 5 minutes.

[24] After removal of the supernatant, 1 mL of an ADSC-BM culture medium was added to the cells, which were then suspended by pipetting.

[25] 9 mL of an ADSC-BM culture medium was further added thereto, and the mixture was stirred.

[26] The number of cells was counted, and the cells were inoculated to a low adhesive 100 mm dish (manufactured by Corning Inc.) and a 96-well plate (manufactured by Corning Inc.) (1.0×10$^6$ cells/dish and 1.0×10$^4$ cells/plate) and spheroid-cultured for 7 days in an incubator (37° C., 5% CO$_2$).

2-1-2 Immunofluorescent Staining Method

The hADSC cells spheroid-cultured in a 96-well plate according to the method described in "2-1-1 Culture of hADSC cells and spheroid culture method" were analyzed according to the method described in "1-1-2 Immunofluorescent staining method". Adherent-cultured hADSC cells were used as a control.

2-1-3 mRNA Expression Analysis

The hMSC-BM cells spheroid-cultured in a 100 mm dish according to the method described in "1-1-1 Culture of hMSC-BM cells and spheroid culture method" were analyzed according to the method described in "1-1-3 mRNA expression analysis". Adherent-cultured hADSC cells were used as a control.

2-2 Results

As a result of detecting the expression of 4 types of pluripotent stem cell marker proteins (Nanog, Oct3/4, Sox2, and SSEA3) using the immunofluorescent staining method, the expression of the 4 types of pluripotent stem cell marker proteins was not detected in the control adherent-cultured hADSC cells, whereas the 4 types of pluripotent stem cell marker proteins were detected in the spheroid-cultured hADSC cells (see FIGS. 6 to 9).

As a result of detecting and quantifying the mRNA expression levels of 3 types of pluripotent stem cell marker genes (Nanog, Oct3/4, and Sox2) by use of RT-PCR, the mRNA expression levels of Nanog and Oct3/4 were drastically increased by 23.6 times and 24.0 times, respectively, in the spheroid-cultured hADSC cells compared with the control adherent-cultured hADSC cells (see FIG. 10). Also, the mRNA expression level of Sox2 was not detected in the control adherent-cultured hADSC cells, but was detected in the spheroid-cultured hADSC cells (see FIG. 10). These results indicate that the spheroid culture of the hADSC cells can induce (or isolate) cells expressing a pluripotent stem cell marker.

Reference Example 1

3. Confirmation that Cells Expressing Pluripotent Stem Cell Marker are Obtained by Spheroid Culture of Adherent Mature Cells and Precursor Cells 3-1 Method 3-1-1 Spheroid Culture Method

[hHEP Cells (1 Type of Adherent Mature Cell)]

[1] hHEP cells (manufactured by In Vitro Technologies, Inc.) were taken out of liquid nitrogen and quickly thawed in a hot water bath of 37° C.

[2] The cells were transferred to a 50 mL centrifuge tube.

[3] 25 mL (ice-cold) of a dedicated culture medium for hHEP cells (culture medium for hHEP culture) (see Table 2) was gradually added dropwise to the cells.

[4] The tube was centrifuged at 4° C. (50×g, 3 minutes).

[5] After removal of the supernatant, 5 mL of an ice-cold culture medium for hHEP culture was added to the cells.

[6] The number of cells was counted, and the cells were inoculated to a low adhesive 96-well plate (manufactured by Corning Inc.) (1.0×10$^4$ cells/well) and spheroid-cultured for 7 days in an incubator (37° C., 5% CO$_2$) (see "hHEP" in FIG. 11). The cells were inoculated to an adhesive 24-well plate (manufactured by AGC Techno Glass Co., Ltd.) as a control (1.0×10$^5$ cells/well) and adherent-cultured for 7 days in an incubator (37° C., 5% CO$_2$).

[HUVEC, HMVEC, NHEK, NHBE, NHEM, and UASMC Cells (6 Types of Adherent Mature Cells), and NHDF, HSMM, and NHOst Cells (3 Types of Adherent Precursor Cells)]

[1] 16 mL each of dedicated culture media for 6 types of adherent mature cells and 3 types of adherent precursor cells mentioned above (culture media for HUVEC, HMVEC, NHEK, NHDF, NHBE, HSMM, NHEM, UASMC, or NHOst culture) (see Table 2) was added to 75 cm$^2$ flasks, and the culture media were warmed and equilibrated in an incubator (37° C., 5% CO$_2$) (30 minutes or longer).

[2] 6 types of adherent mature cells and 3 types of adherent precursor cells (all manufactured by Lonza Group Ltd.) mentioned above were taken out of liquid nitrogen, quickly thawed in a hot water bath of 37° C., and inoculated to the 75 cm$^2$ flasks supplemented with their respective dedicated culture media for the 9 types of cells (2500 to 10000 cells/cm$^2$).

[3] Within 24 hour after inoculation, the culture media were replaced. Subsequently, the culture media were replaced every 1 day to 3 days.
[4] After removal of the culture media, 15 mL of HBSS (manufactured by Lonza Group Ltd.) was added to the cells. The cells were rinsed, followed by the removal of HBSS. DPBS(−) was used instead of HBSS for the HSMM cells. Also, PBS(−) was used instead of HBSS for the NHEM cells.
[5] 6 mL of trypsin/EDTA (manufactured by Lonza Group Ltd.) was added to the cells, which were then treated for 5 minutes.
[6] 12 mL of TNS (manufactured by Lonza Group Ltd.) was added thereto for neutralization.
[7] The cells were placed in 50 mL centrifuge tubes.
[8] Each of the flasks was thoroughly washed by the addition of 5 mL of HBSS. DPBS(−) was used instead of HBSS for the HSMM cells. Also, PBS(−) was used instead of HBSS for the NHEM cells.
[9] Centrifugation treatment was carried out at 220×g at room temperature for 5 minutes. After removal of the supernatants, ice-cold media (4 to 6 mL per cells recovered from one flask) were added. The step [9] was not carried out for the NHEM cells according to the recommended protocol.
[10] The numbers of cells were counted, and the cells were inoculated to 75 cm² flasks (2500 to 10000 cells/cm²).
[11] The culture media were replaced every 1 day to 3 days.
[12] The steps [4] to [11] were repeated until use in analysis.
[13] The same procedures as in the steps [4] to [9] were carried out.
[14] The numbers of cells were counted, and the cells were inoculated to low adhesive 96-well plates (manufactured by Corning Inc.) (1.0×10⁴ cells/well) and spheroid-cultured for 7 days in an incubator (37° C., 5% $CO_2$) (see "HUVEC", "HMVEC", "NHEK", "NHDF", "NHBE", "HSMM", "NHEM", "UASMC", and "NHOst" in FIG. 11). The cells were inoculated to adhesive 24-well plates (manufactured by Corning Inc.) as controls (1.0×10⁵ cells/well) and adherent-cultured for 7 days in an incubator (37° C., 5% $CO_2$).

[hMSC-BM Cells]

hMSC-BM cells were spheroid-cultured in a low adhesive 96-well plate (manufactured by Corning Inc.) according to the method described in "1-1-1 Culture of hMSC-BM cells and spheroid culture method" (see "hMSC-BM" in FIG. 11). The cells were inoculated to an adhesive 24-well plate (manufactured by Corning Inc.) as a control (1.0×10⁵ cells/well) and adherent-cultured for 7 days in an incubator (37° C., 5% $CO_2$).

| Culture medium | Component |
| --- | --- |
| Culture medium for hHEP culture | Basal culture medium for liver cells (manufactured by Lonza Group Ltd., CC-3199) containing HCM set of supplements and factors (manufactured by Lonza Group Ltd., CC-4182) |
| Culture medium for HUVEC culture | Basal culture medium for vascular endothelial cells (manufactured by Lonza Group Ltd., CC-3156) containing EGM set of supplements and factors (manufactured by Lonza Group Ltd., CC-4176) |
| Culture medium for HMVEC culture | Basal culture medium for vascular endothelial cells (manufactured by Lonza Group Ltd., CC-3156) containing EGM-2MV set of supplements and factors (manufactured by Lonza Group Ltd., CC-4147) |
| Culture medium for NHEK culture | Basal culture medium for epidermal keratinocyte cells (manufactured by Lonza Group Ltd., CC-3103) containing KGM-2 set of supplements and factors (manufactured by Lonza Group Ltd., CC-4152) |
| Culture medium for NHDF culture | Basal culture medium for fibroblast cells (manufactured by Lonza Group Ltd., CC-3131) containing FGM-2 set of supplements and factors (manufactured by Lonza Group Ltd., CC-4126) |
| Culture medium for NHBE culture | Basal culture medium for bronchial epithelial cells (manufactured by Lonza Group Ltd., CC-3119) containing SAGM set of supplements and factors (manufactured by Lonza Group Ltd., CC-4124) |
| Culture medium for HSMM culture | Basal culture medium for skeletal muscle myoblast cells (manufactured by Lonza Group Ltd., CC-3246) containing SkGM-2 set of supplements and factors (manufactured by Lonza Group Ltd., CC-3244) |
| Culture medium for NHEM culture | Basal culture medium for melanocytes (manufactured by Lonza Group Ltd., CC-3250) containing MGM-4 set of supplements and factors (manufactured by Lonza Group Ltd., CC-4435) |
| Culture medium for UASMC culture | Basal culture medium for smooth muscle cells (manufactured by Lonza Group Ltd., CC-3181) containing SmGM-2 set of supplements and factors (manufactured by Lonza Group Ltd., CC-4149) |
| Culture medium for NHOst culture | Basal culture medium for osteoblast cells (manufactured by Lonza Group Ltd., CC-3208) containing OGM set of supplements and factors (manufactured by Lonza Group Ltd., CC-4193) |

3-1-2 mRNA Expression Analysis

[1] The cells (16 wells each of the 7 types of adherent mature cells [HUVEC, HMVEC, NHEK, hHEP, NHBE, NHEM, and UASMC cells] and the 3 types of adherent precursor cells [NHDF, HSMM, and NHOst cells] and 24 wells of the hMSC-BM cells) spheroid-cultured according to the method described in "3-1-1 Spheroid culture method" and the control adherent-cultured cells (4 wells each of the 7 types of adherent mature cells and the 3 types of adherent precursor cells and 12 wells of the hMSC-BM cells) were separately recovered into 1.5 mL tubes.
[2] Total RNA was extracted from the cells using RNeasy Mini Kit (manufactured by Qiagen N.V.) and QIA shredder (manufactured by Qiagen N.V.) according to the protocols attached to the products.
[3] The concentration of the extracted total RNA was measured using NanoDrop 2000 (manufactured by Thermo Fisher Scientific, Inc.).
[4] The total RNA was adjusted to 20 μg/mL and dispensed at 3 μL/well (60 ng of RNA) to a 96-well plate (Fast 96 well Reaction plate [manufactured by Applied Biosystems, Inc., #4309169]).
[5] A reaction solution consisting of 1) to 6) given below was prepared using TaqMan RNA-to-CT™ 1-Step Kit (manufactured by Applied Biosystems, Inc., #4392938) and added dropwise to the total RNA-dispensed 96-well plate in order to detect the mRNA expression of 3 types of pluripotent stem cell marker genes (Nanog, Oct3/4, and Sox2) by RT-PCR. GAPDH gene was used as an internal standard.
1) Rnase-free water; 0.5 μL
2) 2× TaqMan RT-PCR Mix; 10 μL (1×)
3) 40× TaqMan RT Enzyme Mix; 0.5 μL
4) Forward Primer; 2.0 μL (900 nM)
5) Reverse Primer; 2.0 μL (900 nM)
6) TaqMan Probe; 2.0 μL (200 nM)

Table 1 shows the nucleotide sequences of the primer sets (aforementioned "Forward Primer" and "Reverse Primer") for amplifying cDNAs of the 4 types of marker genes and the GAPDH gene and the nucleotide sequences of the probes (aforementioned "TaqMan Probe") hybridizing to the amplification (PCR) products.

[6] The mixed solution of the total RNA and the reaction solution prepared in the step [5] was used to carry out real-time RT-PCR with ABI PRISM 7000 Sequence Detection system (manufactured by Applied Biosystems, Inc.) under conditions shown below in 1) to 3).

1) 1 cycle of 48° C. for 15 minutes (reverse transcription reaction of mRNA to cDNA)

2) 1 cycle of 95° C. for 10 minutes (polymerase activation)

3) 40 round-trip cycles of 95° C. for 15 seconds and 60° C. for 1 minute (cDNA amplification with "Forward Primer" and "Reverse Primer")

[7] The number of PCR cycles at which the amount of the PCR product crosses the threshold level (threshold cycle; Ct value) was measured using Baseline software (manufactured by Applied Biosystems, Inc.). The relative Ct values of the cDNA amplification products of the 4 types of marker genes with respect to the Ct value of the cDNA amplification product of the GAPDH gene were determined by the comparative Ct method (delta delta Ct method). From these relative Ct values, the relative cDNA (mRNA) levels of the 4 types of marker genes were calculated (see the ordinates of FIGS. 12 to 14 and Tables 3 to 5).

| | Oct3/4 expression level | | Ratio (Spheroid culture/ adherent culture) |
|---|---|---|---|
| Cell | Adherent culture | Spheroid culture | |
| hHEP | 0.00199 | 0.00406 | 2.04 |
| HUVEC | 0.00202 | 0.130 | 64.4 |
| HMVEC | 0.00500 | 0.0158 | 3.16 |
| NHEK | 0.00035 | 1.076 | 3070 |
| NHDF | 0.00164 | 0.0105 | 6.40 |
| NHBE | 0.00079 | 0.00644 | 8.15 |
| HSMM | 0.00077 | 0.00360 | 4.68 |
| NHEM | 0.00274 | 0.0135 | 4.93 |
| UASMC | 0.00026 | 0.00154 | 5.92 |
| NHOst | 0.00031 | 0.00499 | 16.1 |
| hMSC-BM | 0.00152 | 0.0378 | 24.9 |

| | Nanog expression level | | Ratio (Spheroid culture/ adherent culture) |
|---|---|---|---|
| Cell | Adherent culture | Spheroid culture | |
| hHEP | 0.284 | 2.76 | 9.72 |
| HUVEC | 0.376 | 123 | 327 |
| HMVEC | 0.564 | 9.61 | 17.0 |
| NHEK | 0.154 | 305 | 1980 |
| NHDF | 0.340 | 1.05 | 3.09 |
| NHBE | 0.218 | 0.851 | 3.90 |
| HSMM | 0.111 | 1.97 | 17.7 |
| NHEM | 0.250 | 2.80 | 11.2 |
| UASMC | 0.048 | 1.06 | 22.1 |
| NHOst | 0.106 | 2.65 | 25.0 |
| hMSC-BM | 0.078 | 0.823 | 10.6 |

| | Sox2 expression level | | Sox2 expression ratio (Spheroid culture/ adherent culture) |
|---|---|---|---|
| Cell | Adherent culture | Spheroid culture | |
| hHEP | 0.000036 | 0.000332 | 9.22 |
| HUVEC | 0.000175 | 0.00917 | 52.4 |
| HMVEC | 0.000294 | 0.00107 | 3.64 |
| NHEK | 0.000007 | 0.0876 | 12500 |
| NHDF | 0.000144 | 0.000805 | 5.59 |
| NHBE | 0.000548 | 0.0125 | 22.8 |
| HSMM | 0.000026 | 0.000174 | 6.69 |
| NHEM | 0.000300 | 0.00142 | 4.73 |
| UASMC | 0.000015 | 0.000095 | 6.33 |
| NHOst | 0.000017 | 0.000251 | 14.8 |
| hMSC-BM | 0.000014 | 0.000828 | 59.1 |

3-2 Results

As a result of detecting and quantifying the mRNA expression levels of 3 types of pluripotent stem cell marker genes (Nanog, Oct3/4, and Sox2) by use of RT-PCR, the mRNA expression levels of Nanog and Oct3/4 were drastically increased in all of the spheroid-cultured cells (hMSC-BM cells and 7 types of adherent mature cells and 3 types of adherent precursor cells) compared with the control adherent-cultured cells (see FIGS. 12 to 14 and Tables 3 to 5). These results indicate that the spheroid culture of the mesenchymal stem cells (e.g., hMSC-BM cells), as a matter of course, and even the already differentiated adherent mature cells or the adherent precursor cells to differentiate into a particular tissue or cells can induce (or isolate) cells expressing a pluripotent stem cell marker.

Reference Example 2

4. Study on Culture Medium for Spheroid-Culturing Adherent Mature Cells and Precursor Cells—1

Analysis was made on whether change would be found in the expression levels of pluripotent stem cell marker genes in the case of culturing 6 types of adherent mature cells (HUVEC, HMVEC, NHEK, NHBE, NHEM, and UASMC cells) and 3 types of adherent precursor cells (NHDF, HSMM, and NHOst cells) in a culture medium for MSC culture such as an MSCBM culture medium. The 6 types of adherent mature cells and the 3 types of adherent precursor cells were spheroid-cultured by the method described in Reference Example 1 except that the culture media were changed from their respective dedicated culture media to an MSCBM culture medium. As a result, all of the adherent mature cells were shown to have higher mRNA expression levels of 3 types of pluripotent stem cell marker genes (Nanog, Oct3/4, and Sox2) when spheroid-cultured in the MSCBM culture medium than those when spheroid-cultured in their respective dedicated culture media (see FIGS. 15 to 17 and Tables 6 to 8). These results indicate that the spheroid culture of the adherent mature cells or the adherent precursor cells in the MSCBM culture medium more enhances the efficiency of pluripotency acquisition than the spheroid culture of these cells in their respective dedicated culture media.

| | Oct3/4 expression level | | Ratio |
|---|---|---|---|
| Cell | Dedicated culture medium | MSCBM culture medium | (MSCBM culture medium/ dedicated culture medium) |
| HUVEC | 0.130 | 1.41 | 10.8 |
| HMVEC | 0.0158 | 0.436 | 27.6 |

-continued

| Cell | Oct3/4 expression level | | Ratio |
| | Dedicated culture medium | MSCBM culture medium | (MSCBM culture medium/ dedicated culture medium) |
| --- | --- | --- | --- |
| NHEK | 1.08 | 2.13 | 1.97 |
| NHDF | 0.0105 | 0.0480 | 4.57 |
| NHBE | 0.00644 | 1.16 | 180 |
| HSMM | 0.00360 | 0.0446 | 12.4 |
| NHEM | 0.0135 | 0.0558 | 4.13 |
| UASMC | 0.00154 | 0.00499 | 3.24 |
| NHOst | 0.0126 | 0.0215 | 1.71 |

| Cell | Nanog expression level | | Ratio |
| | Dedicated culture medium | MSCBM culture medium | (MSCBM culture medium/ dedicated culture medium) |
| --- | --- | --- | --- |
| HUVEC | 123 | 989 | 8.04 |
| HMVEC | 9.61 | 377 | 39.2 |
| NHEK | 305 | 2510 | 8.23 |
| NHDF | 1.05 | 3.34 | 3.18 |
| NHBE | 0.851 | 833 | 979 |
| HSMM | 1.97 | 18.1 | 9.19 |
| NHEM | 2.80 | 41.6 | 14.9 |
| UASMC | 1.06 | 2.65 | 2.5 |
| NHOst | 2.13 | 4.41 | 2.07 |

| Cell | Sox2 expression level | | Ratio |
| | Dedicated culture medium | MSCBM culture medium | (MSCBM culture medium/ dedicated culture medium) |
| --- | --- | --- | --- |
| HUVEC | 0.00917 | 0.110 | 12.0 |
| HMVEC | 0.00107 | 0.0241 | 22.5 |
| NHEK | 0.0876 | 0.124 | 1.42 |
| NHDF | 0.000805 | 0.00370 | 4.60 |
| NHBE | 0.0125 | 0.0652 | 5.22 |
| HSMM | 0.000174 | 0.00200 | 11.5 |
| NHEM | 0.00142 | 0.00487 | 3.43 |
| UASMC | 0.000095 | 0.000251 | 2.64 |
| NHOst | 0.000782 | 0.00155 | 1.98 |

Example 3

5. Study on Culture Medium for Spheroid-Culturing hMSC-BM Cells—1

Analysis was made on whether change would be found in the expression levels of pluripotent stem cell marker genes in the case of culturing hMSC-BM cells in a serum-free physiological aqueous solution. The hMSC-BM cells were spheroid-cultured in an infusion solution (ELNEOPA No. 2 Injection [manufactured by Otsuka Pharmaceutical Factory, Inc.] diluted 100-fold with BICANATE Injection [manufactured by Otsuka Pharmaceutical Factory, Inc.]) instead of the MSCBM culture medium. As a result, the increased mRNA expression levels of 3 types of pluripotent stem cell marker genes (Nanog, Oct3/4, and Sox2) were shown (see FIG. 18 and Table 9). These results indicate that the spheroid culture of the mesenchymal stem cells (e.g., hMSC-BM cells) in the serum-free physiological aqueous solution such as an infusion solution more enhances the efficiency of pluripotency acquisition than the spheroid culture of the cells in the culture medium for mesenchymal stem cell culture such as an MSCBM culture medium.

| Gene | Culture medium for hMSC | Infusion solution | Ratio (Infusion solution/ culture medium for hMSC) |
| --- | --- | --- | --- |
| Oct 3/4 | 0.0378 | 0.0822 | 2.17 |
| Nanog | 0.823 | 2.16 | 2.62 |
| Sox2 | 0.000828 | 0.00309 | 3.73 |

Reference Example 3

6. Study on Culture Medium for Spheroid-Culturing Adherent Mature Cells—2

Analysis was made on whether change would be found in the expression levels of pluripotent stem cell marker genes in the case of culturing adherent mature cells in a serum-free physiological aqueous solution. HUVEC cells were spheroid-cultured for 6 days in an infusion solution (ELNEOPA No. 2 Injection [manufactured by Otsuka Pharmaceutical Factory, Inc.] diluted 100-fold with BICANATE Injection [manufactured by Otsuka Pharmaceutical Factory, Inc.]) instead of the culture medium for HUVEC culture (see FIG. 19A). As a result, the increased mRNA expression levels of 3 types of pluripotent stem cell marker genes (Nanog, Oct3/4, and Sox2) were shown (see FIG. 19B and Table 10). Also, NHEK cells were spheroid-cultured for 6 days in the aforementioned infusion solution instead of the culture medium for NHEK culture (see FIG. 20A). Similarly, the increased mRNA expression levels of 3 types of pluripotent stem cell marker genes (Nanog, Oct3/4, and Sox2) were shown (see FIG. 20B and Table 11). These results indicate that the spheroid culture of the adherent mature cells in the serum-free physiological aqueous solution such as an infusion solution more enhances the efficiency of pluripotency acquisition than the spheroid culture of these cells in their respective dedicated culture media.

| Gene | Culture medium for HUVEC | Infusion solution | Ratio (Infusion solution/ culture medium for HUVEC) |
| --- | --- | --- | --- |
| Oct 3/4 | 0.104 | 0.925 | 8.89 |
| Nanog | 65.1 | 512 | 7.86 |
| Sox2 | 0.00685 | 0.0294 | 4.29 |

| Gene | Culture medium for NHEK | Infusion solution | Ratio (Infusion solution/ culture medium for NHEK) |
| --- | --- | --- | --- |
| Oct 3/4 | 0.516 | 1.26 | 2.44 |
| Nanog | 315 | 1320 | 4.19 |
| Sox2 | 0.0399 | 0.0991 | 2.48 |

Example 4

7. Study on Culture Medium for Spheroid-Culturing hMSC-BM Cells—2

Analysis was made on whether change would be found in the expression levels of pluripotent stem cell marker genes in the case of culturing hMSC-BM cells in complete suspension by improving the viscosity of a culture medium using a polysaccharide. The hMSC-BM cells were spheroid-cultured for 7 days in an MSCBM culture medium containing gellan gum (0.02% deacylated gellan gum [manufactured by Sansho Co., Ltd., CG-LA]), the increased mRNA expression level of a pluripotent stem cell marker gene (Nanog) was shown as compared with when the cells were spheroid-cultured in an MSCBM culture medium free from gellan gum (see FIG. 21A). These results suggest that the spheroid culture of the hMSC-BM cells in the culture medium containing gellan gum improved the suspension of the spheroid and enhanced the efficiency of pluripotency acquisition.

Also, the hMSC-BM cells were spheroid-cultured for 1 day in a 96-well plate by the method described in Example 1 to form a spheroid, followed by spheroid culture for 7 days in an MSCBM culture medium containing gellan gum (0.02% deacylated gellan gum [Kelcogel®] [manufactured by Sansho Co., Ltd., CG-LA]), guar gum (0.02% guar gum [manufactured by San-Ei Gen F.F.I., Inc., D-2029]), xanthan gum (0.02% xanthan gum [manufactured by San-Ei Gen F.F.I., Inc., NXG-C]), or dextran (10% dextran 40 [manufactured by Meito Sangyo Co., Ltd.]) (see FIG. 21B). As a result, the increased mRNA expression level of a pluripotent stem cell marker gene (Nanog) was shown in the cells spheroid-cultured in the MSCBM culture medium containing dextran compared with the cells spheroid-cultured in the MSCBM culture medium free from dextran (see FIG. 21B). These results suggest that the spheroid culture of the spheroid of hMSC-BM cells in the culture medium containing dextran improved the suspension of the spheroid and enhanced the efficiency of pluripotency acquisition.

Example 5

8. Analysis on Multilineage Potential of Spheroid of hMSC-BM Cells

In order to analyze the multilineage potential of a spheroid of hMSC-BM cells, the spheroid of hMSC-BM cells was subcultured (spheroid-cultured) according to the method described in "8-1-1 Subculture method after spheroid culture" below and then subjected to differentiation induction treatment into 4 types of organ or tissue (neuronal, liver, heart muscle, and fat) cells according to the method described in "8-1-2 Differentiation induction method by suspension culture" or "8-1-3 Differentiation induction method by adherent culture" below.

8-1 Method 8-1-1 Subculture Method after Spheroid Culture

[1] The spheroid of hMSC-BM cells (corresponding to one 96-well plate) prepared according to the method described in "1-1-1 Culture of hMSC-BM cells and spheroid culture method" was recovered into a 50 mL tube.
[2] The tube was left standing at room temperature for 5 minutes, and then, the supernatant (culture medium) was slowly discarded so as not to aspirate the spheroid and so as to bring the remaining amount of the culture medium to 1 mL or smaller.
[3] After addition of 30 mL of PBS(−) (manufactured by Life Technologies, Inc., 14190144), the tube was left standing for 5 minutes, and then, the supernatant (culture medium) was slowly discarded in the same way as above.
[4] After addition of 2 mL of trypsin/EDTA (manufactured by Lonza Group Ltd.), the tube was left standing for 10 minutes in a water bath of 37° C.
[5] The trypsin treatment was terminated by the addition of 2 mL of an hMSC-BM culture medium (manufactured by Lonza Group Ltd., PT-3001), and then, the spheroid was gradually dispersed 3 to 5 times using P1000 pipette.
[6] Centrifugation treatment was carried out at 600 g at room temperature for 5 minutes. After removal of the supernatant, the cells were suspended by the addition of mL of ReproFF (manufactured by ReproCELL Inc., RCHEMD004) supplemented with 5 ng/mL bFGF (manufactured by ReproCELL Inc., RCHEOT002) (hereinafter, referred to as "FF+bFGF culture medium").
[7] The cells were inoculated to a 96-well plate (manufactured by Corning Inc.) and subcultured (spheroid-cultured) in an incubator (37° C., 5% $CO_2$).
[8] After 4 days, 70 μL/well of the FF+bFGF culture medium was removed, and the culture medium was replaced by the addition of 100 μL of a fresh FF+bFGF culture medium, followed by further subculture (spheroid culture) for 7 days.

8-1-2 Differentiation Induction Method by Suspension Culture

[1] 70 μL/well of the FF+bFGF culture medium was removed from the spheroid of hMSC-BM cells prepared according to the method described in "8-1-1 Subculture method after spheroid culture", and 100 μL each of 5 types of culture media for differentiation induction (see Tables 12 to 16) was freshly added thereto.
[2] The cells were suspension-cultured for 7 days in an incubator (37° C., 5% $CO_2$).
[3] 80 μL/well of the culture medium was removed, and 100 μL each of 5 types of culture media for differentiation induction (see Tables 12 to 16) was freshly added thereto, followed by further suspension culture for 7 days. For samples to be analyzed by the immunostaining method and the oil red staining method, the cells were then suspension-cultured for 7 days, then inoculated to a 96-well plate (manufactured by TPP Techno Plastic Products AG, 92096), and adherent-cultured for 1 day in an incubator (37° C., 5% $CO_2$).

8-1-3 Differentiation Induction Method by Adherent Culture

[1] The spheroid of hMSC-BM cells (corresponding to one 96-well plate) prepared according to the method described in "8-1-1 Subculture method after spheroid culture" was recovered into a 50 mL tube.
[2] The tube was left standing at room temperature for 5 minutes, and then, the supernatant (culture medium) was slowly discarded so as not to aspirate the spheroid and so as to bring the remaining amount of the culture medium to 1 mL or smaller.
[3] 30 mL each of 5 types of culture media for differentiation induction (see Tables 12 to 16) was freshly added thereto, and the cells were inoculated to a 6-well plate (manufactured by TPP Techno Plastic Products AG, 92006) and adherent-cultured for 7 days in an incubator (37° C., 5% $CO_2$). For a guideline, one 96-well plate corresponded to 2 wells of a 6-well plate.
[4] Approximately 80% of the culture medium was replaced with a fresh culture medium, followed by further adherent culture for 7 days.

| Culture medium for neuronal cell induction (neural differentiation induction method 1) | | |
|---|---|---|
| Amount of addition | Component | Stock concentration |
| 100 μL | Penicillin + streptomycin (manufactured by Gibco/Thermo Fisher Scientific, Inc., 10378-016) | 100X |
| 10 μL | rh-bFGF (manufactured by PeproTech, Inc., AF-100-18B) | 40 μg/mL |
| 10 μL | Forskolin (manufactured by Sigma-Aldrich Inc., F3917) | 10 mM |
| 10 μL | rh-CNTF (manufactured by Sigma-Aldrich Inc., C3710) | 10 μg/mL |

Culture medium for neuronal cell induction (neural differentiation induction method 1)

| Amount of addition | Component | Stock concentration |
| --- | --- | --- |
| 10 µL | rh-GDNF (manufactured by Sigma-Aldrich Inc., G1777) | 100 µg/mL |
| 1 mL | FBS (obtained from ATCC, 30-2020) | 1X |
| 9 mL | DMEM (manufactured by Gibco/Thermo Fisher Scientific, Inc., 11965-092) | 1X |

Culture medium for neuronal cell induction (neural differentiation induction method 2)

| Amount of addition | Component | Stock concentration |
| --- | --- | --- |
| 200 µL | Penicillin + streptomycin (manufactured by Gibco/Thermo Fisher Scientific, Inc., 10378-016) | 100X |
| 10 µL | rh-Noggin (manufactured by R&D Systems, Inc., 6057-NG-025) | 250 µg/mL |
| 200 µL | N2 supplement (manufactured by Gibco/Thermo Fisher Scientific, Inc., 17502-048) | 100X |
| 400 µL | B27 supplement (manufactured by Gibco/Thermo Fisher Scientific, Inc., 0050129SA) | 50X |
| 20 mL | DMEM/F-1 (manufactured by Gibco/Thermo Fisher Scientific, Inc., 11320-033) | 1X |

Culture medium for liver cell induction

| Amount of addition | Component | Stock concentration |
| --- | --- | --- |
| 100 µL | Penicillin + streptomycin (manufactured by Gibco/Thermo Fisher Scientific, Inc., 10378-016) | 100X |
| 5 µL | rh-bFGF (manufactured by PeproTech, Inc., AF-100-18B) | 40 µg/mL |
| 200 µL | rh-HGF (manufactured by Sigma-Aldrich Inc., H5791) | 1 µg/mL |
| 1 µL | Dexamethasone (manufactured by Sigma-Aldrich Inc., D4902) | 100 µM |
| 10 µL | Transferrin (manufactured by Sigma-Aldrich Inc., T8158) | 55 mg/mL |
| 1 µL | Sodium selenite (manufactured by Wako Pure Chemical Industries, Ltd., 10102-18-8) | 670 µg/mL |
| 10 µL | Insulin (manufactured by Sigma-Aldrich Inc., I9278) | 10 mg/mL |
| 1 mL | FBS (obtained from ATCC, 30-2020) | 1X |
| 10 mL | DMEM (manufactured by Gibco/Thermo Fisher Scientific, Inc., 11885-084) | 1X |

Culture medium for heart muscle cell induction (see document [Lian et al., PNAS 109 (27), 2012])

| Amount of addition | Component | Stock concentration |
| --- | --- | --- |
| 100 µL | Penicillin + streptomycin (manufactured by Gibco/Thermo Fisher Scientific, Inc., 10378-016) | 100X |
| 10 µL | rh-Activin A (manufactured by R&D Systems, Inc., 338-AC-010) | 100 µg/mL |
| 10 µL | rh-BMP4 (manufactured by R&D Systems, Inc., 314-BP-010) | 100 µg/mL |
| 10 mL | RPMI 1640 (manufactured by Gibco/Thermo Fisher Scientific, Inc., 11875-093) | 1X |

Culture medium for fat cell induction (manufactured by Lonza Group Ltd., PT-3004)

| Amount of addition | Component |
| --- | --- |
| 30 mL | Adipogenic induction SingleQuots kit |
| 170 mL | Adipogenic Induction Medium |

8-1-4 Immunofluorescent Staining Method

The cells induced to differentiate according to the method described in "8-1-2 Differentiation induction method by suspension culture" or "8-1-3 Differentiation induction method by adherent culture" were analyzed for the expression of 3 types of differentiation marker proteins (β tubulin 3 [neuronal cell marker], nestin [neuronal cell marker], and AFP [liver cell marker]) according to the method described in "1-1-2 Immunofluorescent staining method". The cells before differentiation induction (spheroid of hMSC-BM cells) were used as a control. The primary and secondary antibodies used in the detection of the 3 types of differentiation marker proteins are shown in Table 17 below.

| Differentiation marker protein |
| --- |
| β tubulin 3 (neuronal cell marker) |
| Primary antibody: anti-β tubulin 3 antibody (manufactured by Cell Signaling Technology, Inc., SC80016, diluted 100-fold) Secondary antibody: Alexa Fluor 488 anti-mouse antibody [manufactured by Invitrogen Corp., A-11001, diluted 1/1000-fold] |
| Nestin (neuronal cell marker) |
| Primary antibody: anti-nestin antibody (manufactured by Cell Signaling Technology, Inc., SC20978, diluted 100-fold) Secondary antibody: Alexa Fluor 555 anti-rabbit antibody [manufactured by Invitrogen Corp., A-21428, diluted 1/1000-fold] |
| AFP (liver cell marker) |
| Primary antibody: anti-AFP antibody (manufactured by Cell Signaling Technology, Inc., 3903, diluted 100-fold) Secondary antibody: Alexa Fluor 488 anti-mouse antibody [manufactured by Invitrogen Corp., A-11001, diluted 1/1000-fold] |

8-1-5 Oil Red Staining Method

[1] The culture medium was removed from each well containing the cells induced to differentiate into fat cells according to the method described in "8-1-2 Differentiation induction method by suspension culture" or "8-1-3 Differentiation induction method by adherent culture".

[2] PBS was adjusted to pH 7.4 by the addition of 10% (v/v) formalin (10% formalin [manufactured by Wako Pure Chemical Industries, Ltd.]/PBS [pH 7.4]) and then stored at 4° C.

[3] 0.5% (v/v) Oil red O (manufactured by Wako Pure Chemical Industries, Ltd.) was added to isopropanol (manufactured by Wako Pure Chemical Industries, Ltd.), and the mixture was well stirred using a stirrer to prepare a 0.5% Oil red O/Isopropanol solution.

[4] Cold 10% formalin/PBS (approximately 250 μL/well) was added to each well containing the culture medium at a ratio of 2:1, followed by incubation at room temperature for 20 minutes.

[5] The 0.5% Oil red O/Isopropanol solution and distilled water were mixed at a ratio of 3:2 and incubated at room temperature for 10 minutes.

[6] After removal of the culture medium, 400 μL of fresh cold 10% formalin/PBS was added to each well, followed by incubation at room temperature for 1 hour.

[7] After removal of the formalin solution, each well was washed with distilled water (manufactured by Otsuka Pharmaceutical Factory, Inc.) twice with care to prevent the cells from being dissociated. Distilled water remaining in the well was removed using a pipette.

[8] After staining, the cells were washed with distilled water twice.

[9] Cell images were taken using Olympus IX-70 (manufactured by Olympus Corp.).

8-1-6 mRNA Expression Analysis

The cells induced to differentiate according to the method described in "8-1-2 Differentiation induction method by suspension culture" or "8-1-3 Differentiation induction method by adherent culture" were subjected to mRNA expression analysis on 4 types of differentiation marker genes (Musashi [neural progenitor cell marker], MAP2 [neuronal cell marker], GATA4 [heart muscle cell marker], and LPL [fat cell marker]) according to the method described in "3-1-2 mRNA expression analysis". The cells before differentiation induction (spheroid of hMSC-BM cells before subculture and after subculture) were used as a control. Table 18 shows the nucleotide sequences of the primer sets ("Forward Primer" and "Reverse Primer") for amplifying cDNAs of the 5 types of differentiation marker genes and the nucleotide sequences of the probes ("TaqMan Probe") hybridizing to the amplification (PCR) products. FIGS. 24, 26B, and 27D and Tables 19 to 21 show the relative cDNA (mRNA) levels of the 5 types of differentiation marker genes with respect to the cDNA amplification product of the GAPDH gene.

| Primer or probe name | | Nucleotide sequence |
|---|---|---|
| Human Musashi (AB012851.1) | | |
| Musashi | [Forward Primer] | 5'-GGGTTTCGGCTT CGTCACT-3' (SEQ ID NO: 13) |
| Musashi | [Reverse Primer] | 5'-CGATTGCGCCAG CACTTTAT-3' (SEQ ID NO: 14) |
| Musashi | [TaqMan Probe] | 5'-CATGGACCAGGC GGG-3' (SEQ ID NO: 15) |
| Human MAP2 (NM_002374.3) | | |
| MAP2 | [Forward Primer] | 5'-CCATTGCATGAA ACGATCGT-3' (SEQ ID NO: 16) |
| MAP2 | [Reverse Primer] | 5'-TGTCTGAGCGGA AGAGCAGTT-3' (SEQ ID NO: 17) |
| MAP2 | [TaqMan Probe] | 5'-CCCAGGGAGAAT AT-3' (SEQ ID NO: 18) |
| Human GATA4 (NM_002052.3) | | |
| GATA4 | [Forward Primer] | 5'-TTTCCCCTTTGA TTTTTGATCTTC-3' (SEQ ID NO: 19) |
| GATA4 | [Reverse Primer] | 5'-AACGACGGCAAC AACGATAAT-3' (SEQ ID NO: 20) |
| GATA4 | [TaqMan Probe] | 5'-CGACAGTTCCTC CCACG-3' (SEQ ID NO: 21) |
| Human LPL (CR457054.1) | | |
| LPL | [Forward Primer] | 5'-TCCGCGTGATTG CAGAGA-3' (SEQ ID NO: 22) |
| LPL | [Reverse Primer] | 5'-GCTCGTGGGAGC ACTTCACT-3' (SEQ ID NO: 23) |
| LPL | [TaqMan Probe] | 5'-TTGGAGATGTGG ACCAGC-3' (SEQ ID NO: 24) |

| | After neuronal cell differentiation induction | | | | Before neuronal cell differentiation induction | |
|---|---|---|---|---|---|---|
| | Neural differentiation induction method 2 | | Neural differentiation induction method 1 | | Before subculture | After subculture |
| Gene | Suspension | Adherent | Suspension | Adherent | | |
| Musashi | 0.0042 | 0.0506 | 0.0823 | 0.0003 | 0.0015 | 0.0025 |
| MAP2 | 0.0008 | 0.0124 | 0.0107 | 0.0005 | 0.0005 | 0.0005 |

|  | After heart muscle cell differentiation induction | | Before heart muscle cell differentiation induction | |
| --- | --- | --- | --- | --- |
| Gene | Suspension | Adherent | Before subculture | After subculture |
| GATA4 | 0.0201 | 0.130 | 0.0022 | 0.0046 |

|  | After fat cell differentiation induction | | Before fat cell differentiation induction | |
| --- | --- | --- | --- | --- |
| Gene | Suspension | Adherent | Before subculture | After subculture |
| LPL | 2.94 | 2.52 | 0.00003 | 0.00 |

8-2 Results

As a result of carrying out the differentiation induction treatment of a spheroid of hMSC-BM cells into neuronal cells (ectoderm-derived cells) by suspension culture according to the neural differentiation induction method 1, the neuronal cell marker protein (nestin) was expressed (see FIG. 22A), demonstrating that the spheroid differentiates into neuronal cells (see FIG. 22B) expressing mRNAs of the neural progenitor cell marker gene (Musashi) (see "Neural differentiation induction method 1 Suspension" in FIG. 24A and Table 19) and the neuronal cell marker gene (MAP2) (see "Neural differentiation induction method 1 Suspension" in FIG. 24B and Table 19). Also, in the case of carrying out the differentiation induction treatment of the spheroid of hMSC-BM cells into neuronal cells by adherent culture according to the neural differentiation induction method 2, the neuronal cell marker protein (β tubulin 3) was expressed (see FIG. 23A), demonstrating that the spheroid differentiates into neuronal cells (see FIG. 23B) expressing mRNAs of the neural progenitor cell marker gene (Musashi) (see "Neural differentiation induction method 2 Adherent" in FIG. 24A) and the neuronal cell marker gene (MAP2) (see "Neural differentiation induction method 2 Adherent" in FIG. 24B).

The results of carrying out the differentiation induction treatment of the spheroid of hMSC-BM cells into liver cells (endoderm-derived cells) by suspension culture and adherent culture demonstrated that the spheroid differentiates into liver cells (see FIG. 25C) expressing the liver cell marker protein (AFP) (see FIG. 25A).

The results of carrying out the differentiation induction treatment of the spheroid of hMSC-BM cells into heart muscle cells (mesoderm-derived cells) by suspension culture and adherent culture demonstrated that the spheroid differentiates into heart muscle cells (see FIG. 26A) expressing mRNA of the heart muscle cell marker gene (GATA4) (see FIG. 26B and Table 20).

As a result of carrying out the differentiation induction treatment of the spheroid of hMSC-BM cells into fat cells (mesoderm-derived cells) by suspension culture and adherent culture, fat droplets were detected (see FIGS. 27B and 27C), demonstrating that the spheroid differentiates into fat cells (see FIG. 27A) expressing mRNA of the fat cell marker gene (LPL) (see FIG. 27D and Table 21).

The results described above indicate that the spheroid of hMSC-BM cells is cells having the ability to differentiate into cells derived from 3 embryos (ectoderm, endoderm, and mesoderm) (multilineage potential).

Reference Example 4

9. Analysis on Multilineage Potential of Spheroid of Adherent Mature Cells

In order to analyze the multilineage potentials of spheroids of adherent mature cells, 2 types of adherent mature cells (NHEK and HUVEC cells) were inoculated to 96-well plates and spheroid-cultured for 7 days in an MSCBM culture medium to prepare spheroids of adherent mature cells. The prepared spheroids of adherent mature cells were each spheroid-cultured for 1 week in an FF+bFGF culture medium and then subjected to differentiation induction treatment into neuronal cells for 3 weeks by adherent culture according to the neural differentiation induction method 1 in Chamber Slide (manufactured by TPP Techno Plastic Products AG, 92006), followed by analysis on the expression of a neuronal cell marker (TUJ1) according to the method described in "1-1-2 Immunofluorescent staining method" using a primary antibody (anti-TUJ1 antibody [manufactured by EMD Millipore, MAB1637, diluted 100-fold]) and a secondary antibody (Alexa Fluor 555 anti-rabbit antibody [manufactured by Invitrogen Corp., A21422, diluted 1/1000-fold]). As a result, the spheroids of NHEK and HUVEC cells subjected to differentiation induction treatment into neuronal cells were shown to differentiate into neuronal cells expressing the neuronal cell marker protein (TUJ1) (see FIG. 28). These results indicate that the spheroid of adherent mature cells (e.g., NHEK cells and HUVEC cells) is cells having the ability to differentiate at least into ectoderm-derived cells.

Example 6

10. Analysis on Presence or Absence of Ability of Spheroid of hMSC-BM or hADSC Cells to Form Teratoma Since ES cells or iPS cells have an infinite proliferative potential and totipotency, the ES cells or the iPS cells are known to form teratomas when transplanted in an undifferentiated state (see the document "Gropp, et al., PLoS One 7 (9): (2012)"). Thus, a spheroid of hMSC-BM or hADSC cells was analyzed for whether to form teratomas when transplanted.

10-1 Method

The spheroid of hMSC-BM cells ($1 \times 10^6$ cells) prepared according to the method described in Example 1 and the spheroid of hADSC cells ($1 \times 10^6$ cells) prepared according to the method described in Example 2 were each suspended in 0.2 mL of PBS and subcutaneously transplanted to the flank of each female mouse (NOD.CB17-Prkdcscid/J) (manufactured by Charles River Laboratories Japan, Inc.) using a syringe (designated as "MSC Spheroid group" and "ADSC Spheroid group", respectively). For controls, mouse ES cells ($1 \times 10^6$ cells) (manufactured by EMD Millipore, CMSCC050-2A [SCC050]), adherent-cultured hMSC-BM cells ($1 \times 10^6$ cells), or adherent-cultured hADSC cells ($1 \times 10^6$ cells) were suspended in 0.2 mL of PBS and subcutaneously transplanted to the flank of each female mouse (NOD.CB17-Prkdcscid/J) (manufactured by Charles River Laboratories Japan, Inc.) using a syringe (designated as "Positive Control group", "MSC Normal group", and "ADSC Normal group", respectively). A control experiment without cell transplantation was also conducted by the transplantation of PBS (Sham group). At 12 weeks after the transplantation, the mice were euthanized by the cervical dislocation method. When a teratoma was formed, the teratoma was excised. When no teratoma was formed, the transplantation site was excised. The excised tissue was fixed by dipping in a 10% neutral buffered formalin solution and embedded in paraffin. The paraffin-embedded tissue was sliced, and the tissue slices were stained by use of 2 types of staining methods (hematoxylin-eosin staining [HE] method and vimentin staining method). The major axis (L) and minor axis (W) of tumor were measured by microscopic observation using an electronic caliper. The obtained major axis (L) and minor axis (W) of tumor were applied to the expression "Tumor volume (mm$^3$)=L×W$^2$×½" to calculate the tumor volume (see Table 22).

10-2 Results

In the case of transplanting mouse ES cells, teratomas were formed at 3 weeks after transplantation in all of the recipient mice (n=8). By contrast, in the case of transplanting a spheroid of hMSC-BM cells or a spheroid of hADSC cells, teratoma formation was not observed. As a result of pathologic analysis, all of the teratomas formed by the transplantation of the mouse ES cells were constituted by components of 3 germ layers, such as undifferentiated nerve tissues, gastrointestinal tract, and muscle ("Teratoma, immature"), whereas tumors, cell masses, or the like were not observed in the recipient mice given the spheroid of hMSC-BM cells or the spheroid of hADSC cells (see Table 22). Although swelling was confirmed in the mouse of Animal No. 27 in the ADSC Normal group (see Table 22), tumor formation was not observed in this mouse by anatomy and the peritoneum and fat were detected in larger amounts than those of the other mice. The results described above indicate that the spheroid of mesenchymal stem cells (e.g., hMSC-BM cells and hADSC cells) is cells having a very low risk of tumorigenic transformation.

| Organ | Group | Postive Control | | | | | | | | MSC Spheroid | | | | | | | |
|---|---|---|---|---|---|---|---|---|---|---|---|---|---|---|---|---|---|
| Histopathlogical Findings | Animal No. | 1 | 11 | 14 | 15 | 33 | 35 | 36 | 44 | 3 | 7 | 18 | 19 | 22 | 41 | 42 | 46 |
| Subcutaneous tissue Teratoma, immature | | P | P | P | P | P | P | P | P | — | — | — | — | — | — | — | — |
| Organ | Group | MSC Normal | | | | | | | | ADSC Spheroid | | | | | | | |
| Histopathlogical Findings | Animal No. | 6 | 10 | 28 | 31 | 34 | 39 | 40 | 45 | 5 | 8 | 13 | 16 | 21 | 23 | 32 | 43 |
| Subcutaneous tissue Teratoma, immature | | — | — | — | — | — | — | — | — | — | — | — | — | — | — | — | — |

| Organ | Group | ADSC Normal | | | | | | | Sham | | | |
|---|---|---|---|---|---|---|---|---|---|---|---|---|
| Histopathlogical Findings | Animal No. | 4 | 9 | 24 | 25 | 26 | 27 | 30 | 37 | 2 | 29 | 38 | 47 |
| Subcutaneous tissue Teratoma, immature | | — | — | — | — | — | — | — | — | — | — | — | — |

INDUSTRIAL APPLICABILITY

The present invention can inexpensively and conveniently provide highly safe cells for transplantation having a very low risk of tumorigenic transformation and therefore contributes to improvement in safety or cost reduction of regenerative medicine. Moreover, the pluripotent stem cell obtained by the present preparation method 1 or the present preparation method 2 can be allowed to differentiate into each tissue or cell and used in the evaluation of drugs, cosmetics, agricultural chemicals, foods, etc. for their safety, efficacy, or functions. Furthermore, suspension culture can be carried out in a physiological aqueous solution consisting of a single product or a mixed solution of a serum- or serum substitute-free liquid (drug, medical equipment, etc.) administrable to human bodies. As a result, the cells for transplantation are administered to humans while suspended in the physiological aqueous solution used in the culture. Therefore, the necessary safety evaluation (preclinical trial, clinical trial, etc.) of the physiological aqueous solution can be omitted.

The invention claimed is:

1. A method for preparing a pluripotent stem cell, comprising spheroid-culturing mammalian mesenchymal stem cells to form a spheroid of pluripotent stem cells,
   wherein the spheroid-culturing is performed in a solution containing the following (A) or (B):
   (A) gellan gum or a derivative thereof or a salt of these; or
   (B) dextran or a derivative thereof or a salt of these.

2. The method according to claim 1, wherein the mammalian mesenchymal stem cells are human mesenchymal stem cells from bone marrow or human adipose tissue-derived mesenchymal stem cells.

3. The method according to claim 1, wherein the pluripotent stem cell expresses Nanog, Oct3/4, or Sox2.

4. The method according to claim 2, wherein the pluripotent stem cell expresses Nanog, Oct3/4, or Sox2.

* * * * *

```
                        SEQUENCE LISTING

<160> NUMBER OF SEQ ID NOS: 24

<210> SEQ ID NO 1
<211> LENGTH: 21
<212> TYPE: DNA
<213> ORGANISM: Artificial
<220> FEATURE:
<223> OTHER INFORMATION: Inventor: Okairi, Risa
       Inventor: Nishimura, Masuhiro
       Inventor: Wada, Tamaki
<223> OTHER INFORMATION: Human Nanog Forward Primer

<400> SEQUENCE: 1
tggtctcgat ctcctgacct t                                           21

<210> SEQ ID NO 2
<211> LENGTH: 19
<212> TYPE: DNA
<213> ORGANISM: Artificial
<220> FEATURE:
<223> OTHER INFORMATION: Human Nanog Reverse Primer

<400> SEQUENCE: 2
ggctcacgcc tgtaaatcc                                              19

<210> SEQ ID NO 3
<211> LENGTH: 20
<212> TYPE: DNA
<213> ORGANISM: Artificial
<220> FEATURE:
<223> OTHER INFORMATION: Human Nanog TaqMan Probe

<400> SEQUENCE: 3
tgatccaccc gcctcggcct                                             20

<210> SEQ ID NO 4
<211> LENGTH: 20
<212> TYPE: DNA
<213> ORGANISM: Artificial
<220> FEATURE:
<223> OTHER INFORMATION: Human Oct3/4 Forward Primer

<400> SEQUENCE: 4
aacccacact gcagcagatc                                             20

<210> SEQ ID NO 5
<211> LENGTH: 20
<212> TYPE: DNA
<213> ORGANISM: Artificial
<220> FEATURE:
<223> OTHER INFORMATION: Human Oct3/4 Reverse Primer

<400> SEQUENCE: 5
cacactcgga ccacatcctt                                             20

<210> SEQ ID NO 6
<211> LENGTH: 21
<212> TYPE: DNA
<213> ORGANISM: Artificial
<220> FEATURE:
<223> OTHER INFORMATION: Human Oct3/4 TaqMan Probe
```

```
<400> SEQUENCE: 6
ccacatcgcc cagcagcttg g                                              21

<210> SEQ ID NO 7
<211> LENGTH: 16
<212> TYPE: DNA
<213> ORGANISM: Artificial
<220> FEATURE:
<223> OTHER INFORMATION: Human Sox2 Forward Primer

<400> SEQUENCE: 7
gcgcagatgc agccca                                                    16

<210> SEQ ID NO 8
<211> LENGTH: 21
<212> TYPE: DNA
<213> ORGANISM: Artificial
<220> FEATURE:
<223> OTHER INFORMATION: Human Sox2 Reverse Primer

<400> SEQUENCE: 8
tcatgtaggt ctgcgagctg g                                              21

<210> SEQ ID NO 9
<211> LENGTH: 23
<212> TYPE: DNA
<213> ORGANISM: Artificial
<220> FEATURE:
<223> OTHER INFORMATION: Human Sox2 TaqMan Probe

<400> SEQUENCE: 9
caccgctacg acgtgagcgc cct                                            23

<210> SEQ ID NO 10
<211> LENGTH: 21
<212> TYPE: DNA
<213> ORGANISM: Artificial
<220> FEATURE:
<223> OTHER INFORMATION: Human GAPDH Forward Primer

<400> SEQUENCE: 10
catgggtgtg aaccatgaga a                                              21

<210> SEQ ID NO 11
<211> LENGTH: 21
<212> TYPE: DNA
<213> ORGANISM: Artificial
<220> FEATURE:
<223> OTHER INFORMATION: Human GAPDH Reverse Primer

<400> SEQUENCE: 11
ggtcatgagt ccttccacga t                                              21

<210> SEQ ID NO 12
<211> LENGTH: 28
<212> TYPE: DNA
<213> ORGANISM: Artificial
<220> FEATURE:
<223> OTHER INFORMATION: Human GAPDH TaqMan Probe

<400> SEQUENCE: 12
aacagcctca agatcatcag caatgcct                                       28

<210> SEQ ID NO 13
```

```
<211> LENGTH: 19
<212> TYPE: DNA
<213> ORGANISM: Artificial
<220> FEATURE:
<223> OTHER INFORMATION: Human Musashi Forward Primer

<400> SEQUENCE: 13
gggtttcggc ttcgtcact                                            19

<210> SEQ ID NO 14
<211> LENGTH: 20
<212> TYPE: DNA
<213> ORGANISM: Artificial
<220> FEATURE:
<223> OTHER INFORMATION: Human Musashi Reverse Primer

<400> SEQUENCE: 14
cgattgcgcc agcactttat                                           20

<210> SEQ ID NO 15
<211> LENGTH: 15
<212> TYPE: DNA
<213> ORGANISM: Artificial
<220> FEATURE:
<223> OTHER INFORMATION: Human Musashi TaqMan Probe

<400> SEQUENCE: 15
catggaccag gcggg                                                15

<210> SEQ ID NO 16
<211> LENGTH: 20
<212> TYPE: DNA
<213> ORGANISM: Artificial
<220> FEATURE:
<223> OTHER INFORMATION: Human MAP2 Forward Primer

<400> SEQUENCE: 16
ccattgcatg aaacgatcgt                                           20

<210> SEQ ID NO 17
<211> LENGTH: 21
<212> TYPE: DNA
<213> ORGANISM: Artificial
<220> FEATURE:
<223> OTHER INFORMATION: Human MAP2 Reverse Primer

<400> SEQUENCE: 17
tgtctgagcg gaagagcagt t                                         21

<210> SEQ ID NO 18
<211> LENGTH: 21
<212> TYPE: DNA
<213> ORGANISM: Artificial
<220> FEATURE:
<223> OTHER INFORMATION: Human MAP2 Reverse Primer

<400> SEQUENCE: 18
tgtctgagcg gaagagcagt t                                         21

<210> SEQ ID NO 19
<211> LENGTH: 24
<212> TYPE: DNA
<213> ORGANISM: Artificial
<220> FEATURE:
<223> OTHER INFORMATION: Human GATA4 Forward Primer

<400> SEQUENCE: 19
```

```
tttcccttt gatttttgat cttc                                                24

<210> SEQ ID NO 20
<211> LENGTH: 21
<212> TYPE: DNA
<213> ORGANISM: Artificial
<220> FEATURE:
<223> OTHER INFORMATION: Human GATA4 Reverse Primer

<400> SEQUENCE: 20
aacgacggca acaacgataa t                                                  21

<210> SEQ ID NO 21
<211> LENGTH: 17
<212> TYPE: DNA
<213> ORGANISM: Artificial
<220> FEATURE:
<223> OTHER INFORMATION: Human GATA4 TaqMan Probe

<400> SEQUENCE: 21
cgacagttcc tcccacg                                                       17

<210> SEQ ID NO 22
<211> LENGTH: 18
<212> TYPE: DNA
<213> ORGANISM: Artificial
<220> FEATURE:
<223> OTHER INFORMATION: Human LPL Forward Primer

<400> SEQUENCE: 22
tccgcgtgat tgcagaga                                                      18

<210> SEQ ID NO 23
<211> LENGTH: 20
<212> TYPE: DNA
<213> ORGANISM: Artificial
<220> FEATURE:
<223> OTHER INFORMATION: Human LPL Reverse Primer

<400> SEQUENCE: 23
gctcgtggga gcacttcact                                                    20

<210> SEQ ID NO 24
<211> LENGTH: 18
<212> TYPE: DNA
<213> ORGANISM: Artificial
<220> FEATURE:
<223> OTHER INFORMATION: Human LPL TaqMan Probe

<400> SEQUENCE: 24
ttggagatgt ggaccagc                                                      18
```